US009241696B2

(12) United States Patent
Mehl

(10) Patent No.: US 9,241,696 B2
(45) Date of Patent: Jan. 26, 2016

(54) CLOSURE DEVICE

(75) Inventor: Douglas H. Mehl, Redwood City, CA (US)

(73) Assignee: ABBOTT VASCULAR INC., Santa Clara, CA (US)

( * ) Notice: Subject to any disclaimer, the term of this patent is extended or adjusted under 35 U.S.C. 154(b) by 317 days.

(21) Appl. No.: 12/608,773

(22) Filed: Oct. 29, 2009

(65) Prior Publication Data

US 2010/0114156 A1 May 6, 2010

Related U.S. Application Data

(60) Provisional application No. 61/109,822, filed on Oct. 30, 2008, provisional application No. 61/143,748, filed on Jan. 9, 2009.

(51) Int. Cl.
*A61B 17/08* (2006.01)
*A61B 17/00* (2006.01)
*A61B 19/00* (2006.01)

(52) U.S. Cl.
CPC ... *A61B 17/0057* (2013.01); *A61B 2017/00575* (2013.01); *A61B 2017/00592* (2013.01); *A61B 2017/00606* (2013.01); *A61B 2017/00619* (2013.01); *A61B 2017/00623* (2013.01); *A61B 2017/00654* (2013.01); *A61B 2017/00659* (2013.01); *A61B 2017/00986* (2013.01); *A61B 2017/00991* (2013.01); *A61B 2019/4857* (2013.01)

(58) Field of Classification Search
CPC ............... A61B 17/0057; A61B 2017/00991; A61B 2017/00986; A61B 2017/00606; A61B 2017/00623

USPC .......................................... 606/213, 215–218
See application file for complete search history.

(56) References Cited

U.S. PATENT DOCUMENTS

| 287,046 A | 10/1883 | Norton |
| 438,400 A | 10/1890 | Brennen |
| 556,082 A | 3/1896 | Boeddinghaus |
| 1,088,393 A | 2/1914 | Backus |
| 1,123,290 A | 1/1915 | Von Herff |
| 1,242,139 A | 10/1917 | Callahan |
| 1,331,401 A | 2/1920 | Summers |
| 1,480,935 A | 1/1924 | Gleason |
| 1,596,004 A | 8/1926 | De Bengoa |

(Continued)

FOREIGN PATENT DOCUMENTS

| AU | 2003297432 | 7/2004 |
| CA | 2 339 060 | 2/2000 |

(Continued)

OTHER PUBLICATIONS

U.S. Appl. No. 10/667,144, Oct. 28, 2011, Notice of Allowance.

(Continued)

*Primary Examiner* — Julian W Woo
*Assistant Examiner* — Shaun L David
(74) *Attorney, Agent, or Firm* — Workman Nydegger; Randy Shen

(57) ABSTRACT

A closure device for closing an opening in tissue is provided. The closure device according the present invention includes a delivery system for deploying a closure element, wherein the closure element is movable between a delivery configuration and a deployed configuration to close an opening in tissue. The closure device of the present invention may further include a charge of hemostatic material.

19 Claims, 10 Drawing Sheets

(56) References Cited

U.S. PATENT DOCUMENTS

| | | |
|---|---|---|
| 1,647,958 A | 11/1927 | Ciarlante |
| 1,880,569 A | 10/1932 | Weis |
| 2,087,074 A | 7/1937 | Tucker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,682,180 A | 8/1972 | McFarlane |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A * | 4/1975 | King et al. .............. 606/232 |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,570,633 A | 2/1986 | Golden |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A * | 6/1989 | Landymore et al. .......... 606/215 |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 E | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,011,487 A | 4/1991 | Shichman |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |

(56) References Cited

U.S. PATENT DOCUMENTS

| | | |
|---|---|---|
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,259 A | 12/1992 | Inoue |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Janota |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,322,694 A | 6/1994 | Sixsmith |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,392,978 A | 2/1995 | Velez et al. |
| 5,395,030 A | 3/1995 | Kuramoto et al. |
| 5,404,621 A | 4/1995 | Heinke |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A * | 9/1995 | Lock et al. ............ 606/213 |
| 5,454,413 A | 10/1995 | Morelli |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,484,420 A | 1/1996 | Russo |
| 5,486,195 A | 1/1996 | Myers et al. |
| 5,496,332 A | 3/1996 | Sierra et al. |
| 5,497,933 A | 3/1996 | DeFonzo et al. |
| 5,507,744 A | 4/1996 | Tay et al. |
| 5,507,755 A | 4/1996 | Gresl et al. |
| 5,510,115 A | 4/1996 | Breillatt, Jr. et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,626,614 A | 5/1997 | Hart |
| 5,634,936 A * | 6/1997 | Linden et al. ............ 606/213 |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,935 A | 9/1997 | Rosenman et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |

(56) References Cited

U.S. PATENT DOCUMENTS

| | | | |
|---|---|---|---|
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,697,943 A | 12/1997 | Sauer et al. |
| 5,700,273 A | 12/1997 | Buelna et al. |
| 5,709,224 A | 1/1998 | Behl et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,736 A | 4/1998 | Volk |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |
| 5,755,727 A | 5/1998 | Kontos |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A * | 8/1998 | Stevens et al. ............... 606/213 |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,217 A | 11/1998 | Ryan |
| 5,830,221 A | 11/1998 | Stein et al. |
| 5,833,698 A | 11/1998 | Hinchliffe et al. |
| 5,843,164 A | 12/1998 | Frantzen et al. |
| 5,843,167 A | 12/1998 | Dwyer et al. |
| 5,845,657 A | 12/1998 | Carberry et al. |
| 5,853,421 A | 12/1998 | Leschinsky et al. |
| 5,853,422 A * | 12/1998 | Huebsch et al. ............... 606/213 |
| 5,855,312 A | 1/1999 | Toledano |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,904,703 A | 5/1999 | Gilson |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,928,260 A | 7/1999 | Chin et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,023 A | 10/1999 | Tanner et al. |
| 5,976,161 A | 11/1999 | Kirsch et al. |
| 5,976,174 A | 11/1999 | Ruiz |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri |
| 6,024,756 A * | 2/2000 | Huebsch et al. ............... 606/213 |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,074,395 A | 6/2000 | Trott et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,095,155 A | 8/2000 | Criscuolo |
| 6,102,271 A | 8/2000 | Longo et al. |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A * | 9/2000 | Huebsch et al. ............... 606/213 |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |

(56) References Cited

U.S. PATENT DOCUMENTS

| | | | |
|---|---|---|---|
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1* | 1/2001 | Schneidt ............ 606/213 |
| 6,179,849 B1 | 1/2001 | Yencho et al. |
| 6,179,860 B1 | 1/2001 | Fulton, III et al. |
| 6,183,775 B1 | 2/2001 | Ventouras |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,210,418 B1 | 4/2001 | Storz et al. |
| 6,220,248 B1 | 4/2001 | Voegele et al. |
| 6,221,102 B1 | 4/2001 | Baker et al. |
| 6,231,561 B1 | 5/2001 | Frazier et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,287,335 B1 | 9/2001 | Drasler et al. |
| 6,290,674 B1 | 9/2001 | Roue et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1* | 3/2002 | Neuss et al. ............ 606/213 |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,544,230 B1 | 4/2003 | Flaherty et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,596,013 B2 | 7/2003 | Yang et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,626,930 B1 | 9/2003 | Allen et al. |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,784 B2 | 8/2004 | Ginn |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |

(56) References Cited

U.S. PATENT DOCUMENTS

| | | | |
|---|---|---|---|
| 6,837,906 B2 | 1/2005 | Ginn | |
| 6,846,319 B2 | 1/2005 | Ginn et al. | |
| 6,849,078 B2 | 2/2005 | Durgin et al. | |
| 6,860,895 B1 | 3/2005 | Akerfeldt et al. | |
| 6,890,343 B2 | 5/2005 | Ginn et al. | |
| 6,896,687 B2 | 5/2005 | Dakov | |
| 6,896,692 B2 | 5/2005 | Ginn et al. | |
| 6,904,647 B2 | 6/2005 | Byers, Jr. | |
| 6,913,607 B2 | 7/2005 | Ainsworth et al. | |
| 6,926,723 B1 | 8/2005 | Mulhauser et al. | |
| 6,926,731 B2 | 8/2005 | Coleman et al. | |
| 6,929,634 B2 | 8/2005 | Dorros et al. | |
| 6,942,641 B2 | 9/2005 | Seddon | |
| 6,942,674 B2 | 9/2005 | Belef et al. | |
| 6,942,691 B1 | 9/2005 | Chuter | |
| 6,964,668 B2 | 11/2005 | Modesitt et al. | |
| 6,969,391 B1 | 11/2005 | Gazzani | |
| 6,969,397 B2 | 11/2005 | Ginn | |
| 6,984,238 B2 | 1/2006 | Gifford, III et al. | |
| 6,989,003 B2 | 1/2006 | Wing et al. | |
| 6,989,016 B2 | 1/2006 | Tallarida et al. | |
| 7,001,398 B2 | 2/2006 | Carley et al. | |
| 7,001,400 B1 | 2/2006 | Modesitt et al. | |
| 7,008,435 B2 | 3/2006 | Cummins | |
| 7,008,439 B1 | 3/2006 | Janzen et al. | |
| 7,025,776 B1* | 4/2006 | Houser et al. | 606/213 |
| 7,033,379 B2 | 4/2006 | Peterson | |
| 7,060,084 B1 | 6/2006 | Loshakove et al. | |
| 7,063,711 B1 | 6/2006 | Loshakove et al. | |
| 7,074,232 B2 | 7/2006 | Kanner et al. | |
| 7,076,305 B2 | 7/2006 | Imran et al. | |
| 7,083,635 B2 | 8/2006 | Ginn | |
| 7,087,064 B1 | 8/2006 | Hyde | |
| 7,108,709 B2 | 9/2006 | Cummins | |
| 7,111,768 B2 | 9/2006 | Cummins et al. | |
| 7,112,225 B2 | 9/2006 | Ginn | |
| 7,144,411 B2 | 12/2006 | Ginn et al. | |
| 7,163,551 B2 | 1/2007 | Anthony et al. | |
| 7,169,158 B2 | 1/2007 | Sniffin et al. | |
| 7,169,164 B2 | 1/2007 | Borillo et al. | |
| 7,211,101 B2 | 5/2007 | Carley et al. | |
| 7,220,268 B2 | 5/2007 | Blatter | |
| 7,261,716 B2 | 8/2007 | Strobel et al. | |
| 7,306,614 B2 | 12/2007 | Weller et al. | |
| 7,311,720 B2 | 12/2007 | Mueller et al. | |
| 7,316,704 B2 | 1/2008 | Bagaoisan et al. | |
| 7,316,706 B2 | 1/2008 | Bloom et al. | |
| 7,322,995 B2 | 1/2008 | Beckman et al. | |
| 7,326,230 B2 | 2/2008 | Ravikumar | |
| 7,331,979 B2 | 2/2008 | Khosravi et al. | |
| 7,335,220 B2 | 2/2008 | Khosravi et al. | |
| D566,272 S | 4/2008 | Walberg et al. | |
| 7,361,178 B2 | 4/2008 | Hearn et al. | |
| 7,361,183 B2 | 4/2008 | Ginn | |
| 7,361,185 B2 | 4/2008 | O'Malley et al. | |
| 7,393,363 B2 | 7/2008 | Ginn | |
| 7,396,359 B1 | 7/2008 | Derowe et al. | |
| 7,431,729 B2* | 10/2008 | Chanduszko | 606/213 |
| 7,445,596 B2 | 11/2008 | Kucklick et al. | |
| 7,465,286 B2 | 12/2008 | Patterson et al. | |
| 7,533,790 B1 | 5/2009 | Knodel et al. | |
| 7,582,103 B2 | 9/2009 | Young et al. | |
| 7,582,104 B2* | 9/2009 | Corcoran et al. | 606/215 |
| 7,597,706 B2 | 10/2009 | Kanner et al. | |
| 7,618,427 B2 | 11/2009 | Ortiz et al. | |
| 7,622,628 B2 | 11/2009 | Bergin et al. | |
| 7,645,285 B2 | 1/2010 | Cosgrove et al. | |
| D611,144 S | 3/2010 | Reynolds | |
| 7,678,135 B2 | 3/2010 | Maahs et al. | |
| 7,780,696 B2 | 8/2010 | Daniel et al. | |
| 7,799,042 B2 | 9/2010 | Williamson, IV et al. | |
| 7,806,904 B2 | 10/2010 | Carley et al. | |
| 7,819,895 B2 | 10/2010 | Ginn et al. | |
| 7,841,502 B2 | 11/2010 | Walberg et al. | |
| 7,842,068 B2 | 11/2010 | Ginn | |
| 7,850,709 B2 | 12/2010 | Cummins et al. | |
| 7,850,797 B2 | 12/2010 | Carley et al. | |
| 7,854,810 B2 | 12/2010 | Carley et al. | |
| 7,857,828 B2 | 12/2010 | Jabba et al. | |
| 7,867,249 B2 | 1/2011 | Palermo et al. | |
| 7,875,054 B2 | 1/2011 | LaFontaine | |
| 7,931,671 B2 | 4/2011 | Tenerz | |
| 7,967,842 B2 | 6/2011 | Bakos | |
| 8,103,327 B2 | 1/2012 | Harlev et al. | |
| 8,105,352 B2 | 1/2012 | Egnelöv | |
| 8,172,749 B2 | 5/2012 | Melsheimer | |
| 8,226,666 B2 | 7/2012 | Zarbatany et al. | |
| 8,409,228 B2 | 4/2013 | Blatter et al. | |
| 2001/0007077 A1 | 7/2001 | Ginn et al. | |
| 2001/0021855 A1 | 9/2001 | Levinson | |
| 2001/0031972 A1 | 10/2001 | Robertson et al. | |
| 2001/0031973 A1 | 10/2001 | Nobles et al. | |
| 2001/0044639 A1 | 11/2001 | Levinson | |
| 2001/0046518 A1 | 11/2001 | Sawhney | |
| 2001/0047180 A1 | 11/2001 | Grudem et al. | |
| 2002/0022822 A1 | 2/2002 | Cragg et al. | |
| 2002/0026215 A1 | 2/2002 | Redmond et al. | |
| 2002/0026216 A1 | 2/2002 | Grimes | |
| 2002/0029050 A1 | 3/2002 | Gifford, III et al. | |
| 2002/0038127 A1 | 3/2002 | Blatter et al. | |
| 2002/0042622 A1 | 4/2002 | Vargas et al. | |
| 2002/0049427 A1 | 4/2002 | Wiener et al. | |
| 2002/0058960 A1 | 5/2002 | Hudson et al. | |
| 2002/0062104 A1 | 5/2002 | Ashby et al. | |
| 2002/0077657 A1 | 6/2002 | Ginn et al. | |
| 2002/0082641 A1 | 6/2002 | Ginn et al. | |
| 2002/0095181 A1 | 7/2002 | Beyar | |
| 2002/0099389 A1 | 7/2002 | Michler et al. | |
| 2002/0106409 A1 | 8/2002 | Sawhney et al. | |
| 2002/0107542 A1 | 8/2002 | Kanner et al. | |
| 2002/0133193 A1 | 9/2002 | Ginn et al. | |
| 2002/0151921 A1 | 10/2002 | Kanner et al. | |
| 2002/0151963 A1 | 10/2002 | Brown et al. | |
| 2002/0169475 A1 | 11/2002 | Gainor et al. | |
| 2002/0183786 A1 | 12/2002 | Girton | |
| 2002/0183787 A1 | 12/2002 | Wahr et al. | |
| 2002/0198562 A1 | 12/2002 | Ackerfeldt et al. | |
| 2002/0198589 A1 | 12/2002 | Leong | |
| 2003/0004543 A1 | 1/2003 | Gleeson et al. | |
| 2003/0009180 A1 | 1/2003 | Hinchliffe et al. | |
| 2003/0018358 A1 | 1/2003 | Saadat | |
| 2003/0023248 A1 | 1/2003 | Parodi | |
| 2003/0032981 A1 | 2/2003 | Kanner et al. | |
| 2003/0033006 A1 | 2/2003 | Phillips et al. | |
| 2003/0045893 A1 | 3/2003 | Ginn | |
| 2003/0055455 A1 | 3/2003 | Yang et al. | |
| 2003/0060846 A1 | 3/2003 | Egnelov et al. | |
| 2003/0065358 A1 | 4/2003 | Frecker et al. | |
| 2003/0078598 A1 | 4/2003 | Ginn et al. | |
| 2003/0083679 A1 | 5/2003 | Grudem et al. | |
| 2003/0093096 A1 | 5/2003 | McGuckin et al. | |
| 2003/0093108 A1 | 5/2003 | Avellanet et al. | |
| 2003/0097140 A1 | 5/2003 | Kanner | |
| 2003/0109890 A1 | 6/2003 | Kanner et al. | |
| 2003/0125766 A1 | 7/2003 | Ding | |
| 2003/0139819 A1 | 7/2003 | Beer et al. | |
| 2003/0144695 A1 | 7/2003 | McGuckin, Jr. et al. | |
| 2003/0158577 A1 | 8/2003 | Pantages et al. | |
| 2003/0158578 A1 | 8/2003 | Pantages et al. | |
| 2003/0195504 A1 | 10/2003 | Tallarida et al. | |
| 2003/0195561 A1 | 10/2003 | Carley et al. | |
| 2003/0208211 A1 | 11/2003 | Kortenbach | |
| 2004/0009205 A1 | 1/2004 | Sawhney | |
| 2004/0009289 A1 | 1/2004 | Carley et al. | |
| 2004/0044350 A1 | 3/2004 | Martin et al. | |
| 2004/0049224 A1 | 3/2004 | Buehlmann et al. | |
| 2004/0059376 A1 | 3/2004 | Breuniger | |
| 2004/0068273 A1 | 4/2004 | Fariss et al. | |
| 2004/0073236 A1 | 4/2004 | Carley et al. | |
| 2004/0073255 A1 | 4/2004 | Ginn et al. | |
| 2004/0078053 A1 | 4/2004 | Berg et al. | |
| 2004/0082906 A1 | 4/2004 | Tallarida et al. | |
| 2004/0087985 A1 | 5/2004 | Loshakove et al. | |
| 2004/0092962 A1 | 5/2004 | Thornton et al. | |

(56) References Cited

U.S. PATENT DOCUMENTS

| | | |
|---|---|---|
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0245876 A1 | 11/2005 | Khosravi et al. |
| 2005/0256532 A1 | 11/2005 | Nayak et al. |
| 2005/0267524 A1 | 12/2005 | Chanduszko |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0100664 A1 | 5/2006 | Pai et al. |
| 2006/0142784 A1 | 6/2006 | Kontos |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0195125 A1 | 8/2006 | Sakakine et al. |
| 2006/0206146 A1 | 9/2006 | Tenerez |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0287674 A1 | 12/2006 | Ginn et al. |
| 2066/0293698 | 12/2006 | Douk |
| 2007/0005093 A1 | 1/2007 | Cox |
| 2007/0010851 A1* | 1/2007 | Chanduszko et al. ........ 606/213 |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0078302 A1* | 4/2007 | Ortiz et al. .................... 600/115 |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0149996 A1 | 6/2007 | Coughlin |
| 2007/0167981 A1* | 7/2007 | Opolski ............. A61B 17/0057 606/213 |
| 2007/0172430 A1 | 7/2007 | Brito et al. |
| 2007/0179527 A1 | 8/2007 | Eskuri et al. |
| 2007/0185529 A1* | 8/2007 | Coleman et al. .............. 606/213 |
| 2007/0185530 A1 | 8/2007 | Chin-Chen et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg et al. |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0097509 A1 | 4/2008 | Beyar et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0208225 A1 | 8/2008 | Seibold et al. |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312666 A1 | 12/2008 | Ellingwood et al. |
| 2008/0312667 A1 | 12/2008 | Drasler et al. |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |

(56) References Cited

U.S. PATENT DOCUMENTS

| | | | |
|---|---|---|---|
| 2009/0105728 A1 | 4/2009 | Noda et al. |
| 2009/0112306 A1 | 4/2009 | Bonsignore et al. |
| 2009/0132031 A1 | 5/2009 | Cook et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0171388 A1 | 7/2009 | Dave et al. |
| 2009/0177212 A1 | 7/2009 | Carley et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114159 A1 | 5/2010 | Roorda et al. |
| 2010/0130965 A1 | 5/2010 | Sibbitt, Jr. et al. |
| 2010/0160958 A1 | 6/2010 | Clark |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0217132 A1 | 8/2010 | Ellingwood et al. |
| 2010/0249828 A1 | 9/2010 | Mavani et al. |
| 2011/0066163 A1 | 3/2011 | Cho et al. |
| 2011/0082495 A1 | 4/2011 | Ruiz |
| 2011/0178548 A1 | 7/2011 | Tenerz |
| 2011/0270282 A1 | 11/2011 | Lemke |
| 2012/0035630 A1 | 2/2012 | Roorda |
| 2012/0101520 A1 | 4/2012 | Ginn et al. |
| 2012/0245603 A1 | 9/2012 | Voss |
| 2012/0245623 A1 | 9/2012 | Kariniemi et al. |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |
| 2013/0338708 A1 | 12/2013 | Cummins et al. |
| 2014/0005692 A1 | 1/2014 | Ellingwood et al. |
| 2014/0018850 A1 | 1/2014 | Ellingwood |
| 2014/0142624 A1 | 5/2014 | Pantages et al. |
| 2014/0309686 A1 | 10/2014 | Ginn et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 1 274750 | 11/1989 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |

(56) References Cited

FOREIGN PATENT DOCUMENTS

| | | |
|---|---|---|
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 11/675,462, Dec. 22, 2011, Notice of Allowance.
U.S. Appl. No. 12/393,877, Dec. 13, 2011, Office Action.
U.S. Appl. No. 12/481,377, Jan. 3, 2012, Office Action.
U.S. Appl. No. 12/548,274, Dec. 28, 2011, Office Action.
U.S. Appl. No. 12/684,470, Dec. 20, 2011, Office Action.
U.S. Appl. No. 12/684,562, Dec. 28, 2011, Office Action.
U.S. Appl. No. 12/684,569, Dec. 20, 2011, Office Action.
U.S. Appl. No. 12/897,358, Jan. 12, 2012, Notice of Allowance.
U.S. Appl. No. 12/941,809, Dec. 13, 2011, Office Action.
U.S. Appl. No. 12/945,646, Oct. 26, 2011, Office Action.
U.S. Appl. No. 12/955,859, Dec. 15, 2011, Office Action.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 12/897,358, filed Oct. 4, 2010, Carley.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/961,331, filed Dec. 6, 2010, Voss.
U.S. Appl. No. 12/945,646, filed Nov. 12, 2010, Carley et al.
U.S. Appl. No. 12/966,923, filed Dec. 13, 2010, Cummins et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.

"Hand tool for forming telephone connections—comprises pliers with reciprocably driven ram crimping clip around conductors against anvil", Derwent-ACC-No. 1978-B8090A.

Database WPI; Section PQ, Week 200120; Derwent Publications Ltd., London GB; AN 2001-203165; XP002199926 & ZA 200 100 528 A (Anthony T), Feb. 28, 2001 abstract.

Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.

DL Wessel et al, Outpatient closure of the patent ductus arteriosus, Circulation, May 1988, pp. 1068-1071, vol. 77—No. 5, Department of Anesthesia, Children's Hospital, Boston, MA.

E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.

G Gershony et al, Novel vascular sealing device for closure of percutaneous vascular access sites, Cathet. Cardiovasc. Diagn., Jan. 1998, pp. 82-88, vol. 45.

H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.

Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.

J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.

Jeremy L Gilbert Phd, Wound Closure Biomaterials and Devices, Shock., Mar. 1999, p. 226, vol. 11—No. 3, Institution Northwestern University (editorial review).

Jochen T. Cremer, Md, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.

K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.

Marshall A.C., Lock J.E., Structural and Compliant Anatomy of the Patent Foramen Ovale in Patients Undergoing Transcatheter Closure, Am Heart J Aug. 2000; 140(2); pp. 303-307.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

Inlet Medical Inc. Brochure, pp. 1-2, referencing Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

(56) References Cited

OTHER PUBLICATIONS

Peter Rhee Md et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive. org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, Md, Phd, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum Rpa-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.
Ut Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III Md, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.

(56) References Cited

OTHER PUBLICATIONS

U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Office Action.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/435,104, Jan. 12, 2011, Issue Notification.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/517,004, Nov. 23, 2010, Issue Notification.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/541,083, Dec. 1, 2010, Issue Notification.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/638,115, Dec. 22, 2010, Issue Notification.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/048,503, Dec. 8, 2010, Issue Notification.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/198,811, Oct. 20, 2010, Issue Notification.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.

(56) References Cited

OTHER PUBLICATIONS

U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/406,203, Oct. 6, 2010, Issue Notification.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/852,190, Jun. 24, 2010, Office Action.
U.S. Appl. No. 11/852,190, Nov. 1, 2010, Office Action.
U.S. Appl. No. 11/958,281, Sep. 2, 2010, Office Action.
U.S. Appl. No. 11/958,281, Oct. 8, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 11/959,334, Nov. 10, 2010, Issue Notification.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/114,031, Oct. 5, 2010, Office Action.
U.S. Appl. No. 12/114,031, Nov. 22, 2010, Office Action.
U.S. Appl. No. 12/114,091, Oct. 27, 2010, Office Action.
U.S. Appl. No. 12/114,091, Dec. 17, 2010, Office Action.
U.S. Appl. No. 12/402,398, Mar. 9, 2010, Office Action.
U.S. Appl. No. 12/402,398, May 20, 2010, Office Action.
U.S. Appl. No. 12/402,398, Jan. 24, 2011, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,256, Nov. 23, 2010, Issue Notification.
U.S. Appl. No. 12/403,277, Jul. 8, 2010, Office Action.
U.S. Appl. No. 12/403,277, Oct. 12, 2010, Office Action.
U.S. Appl. No. 12/945,646, Jan. 20, 2011, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 12/338,977, Jan. 19, 2012, Office Action.
U.S. Appl. No. 12/684,569, Jan. 27, 2012, Office Action.
U.S. Appl. No. 11/767,818, Feb. 3, 2012, Notice of Allowance.
U.S. Appl. No. 12/684,542, Jan. 30, 2012, Restriction Requirement.
U.S. Appl. No. 12/941,809, Jan. 30, 2012, Office Action.
U.S. Appl. No. 12/966,923, Feb. 3, 2012, Notice of Allowance.
U.S. Appl. No. 13/017,636, filed Jan. 31, 2011, Carley et al.
U.S. Appl. No. 10/616,832, Jan. 26, 2011, Issue Notification.
U.S. Appl. No. 11/152,562, Jan. 26, 2011, Issue Notification.
U.S. Appl. No. 13/026,989, filed Feb. 14, 2011, Cummins.
U.S. Appl. No. 10/264,306, Feb. 16, 2011, Issue Notification.
U.S. Appl. No. 11/767,818, Feb. 16, 2011, Office Action.
U.S. Appl. No. 13/030,922, filed Feb. 18, 2011, Cummins.
U.S. Appl. No. 10/356,214, Feb. 23, 2011, Issue Notification.
U.S. Appl. No. 12/114,031, Mar. 6, 2012, Office Action.
U.S. Appl. No. 12/135,858, Feb. 16, 2012, Office Action.
U.S. Appl. No. 12/143,020, Feb. 23, 2012, Notice of Allowance.
U.S. Appl. No. 12/548,274, Mar. 2, 2012, Office Action.
U.S. Appl. No. 12/608,769, Feb. 10, 2012, Office Action.
U.S. Appl. No. 12/642,319, Feb. 27, 2012, Office Action.
U.S. Appl. No. 12/684,400, Feb. 13, 2012, Office Action.
U.S. Appl. No. 12/684,562, Feb. 16, 2012, Office Action.
U.S. Appl. No. 12/724,304, Feb. 10, 2012, Office Action.
U.S. Appl. No. 12/897,358, Mar. 5, 2012, Notice of Allowance.
U.S. Appl. No. 12/945,646, Feb. 21, 2012, Notice of Allowance.
U.S. Appl. No. 12/973,204, Mar. 7, 2012, Notice of Allowance.
U.S. Appl. No. 13/039,087, filed Mar. 2, 2011, Palermo et al.
U.S. Appl. No. 11/852,190, Mar. 2, 2011, Office Action.
U.S. Appl. No. 12/122,603, Mar. 3, 2011, Office Action.
U.S. Appl. No. 11/958,281, Mar. 10, 2011, Office Action.
U.S. Appl. No. 11/532,576, Mar. 16, 2011, Issue Notification.
U.S. Appl. No. 11/396,731, Mar. 22, 2011, Office Action.
U.S. Appl. No. 11/427,297, Mar. 21, 2011, Office Action.
U.S. Appl. No. 10/147,774, Apr. 6, 2011, Issue Notification.
U.S. Appl. No. 10/682,459, Apr. 1, 2011, Notice of Allowance.
U.S. Appl. No. 12/403,277, Mar. 31, 2011, Office Action.
U.S. Appl. No. 12/113,851, Mar. 29, 2012, Office Action.
U.S. Appl. No. 12/114,091, Apr. 5, 2012, Office Action.
U.S. Appl. No. 12/403,277, Apr. 3, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/987,792, Mar. 13, 2012, Office Action.
U.S. Appl. No. 12/122,603, Apr. 22, 2011, Office Action.
U.S. Appl. No. 12/113,851, Apr. 27, 2011, Office Action.
U.S. Appl. No. 12/481,377, Apr. 28, 2011, Office Action.
U.S. Appl. No. 13/308,227, filed Nov. 30, 2011, Yibarren.
U.S. Appl. No. 11/390,586, May 3, 2012, Notice of Allowance.
U.S. Appl. No. 12/684,542, Apr. 16, 2012, Office Action.
U.S. Appl. No. 12/688,065, Apr. 26, 2012, Office Action.
U.S. Appl. No. 12/897,358, May 2, 2012, Issue Notification.
U.S. Appl. No. 12/114,031, May 11, 2011, Office Action.
U.S. Appl. No. 12/143,020, May 11, 2011, Office Action.
U.S. Appl. No. 13/112,618, filed May 20, 2011, Gianotti et al.

(56) References Cited

OTHER PUBLICATIONS

U.S. Appl. No. 13/112,631, filed May 20, 2011, Voss.
U.S. Appl. No. 12/955,859, May 26, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 12/481,377, Jun. 21, 2011, Office Action.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/393,877, May 21, 2012, Office Action.
U.S. Appl. No. 12/684,400, May 9, 2012, Office Action.
U.S. Appl. No. 12/941,809, Jun. 1, 2012, Office Action.
U.S. Appl. No. 13/026,989, Jun. 8, 2012, Office Action.
U.S. Appl. No. 12/114,091, Jul. 7, 2011, Office Action.
U.S. Appl. No. 12/945,646, Jul. 6, 2011, Office Action.
U.S. Appl. No. 12/135,858, Jul. 13, 2011, Office Action.
U.S. Appl. No. 12/955,859, Jul. 21, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 10/682,459, Aug. 10, 2011, Issue Notification.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 11/396,731, Sep. 1, 2011, Office Action.
U.S. Appl. No. 13/026,989, Sep. 16, 2011, Office Action.
U.S. Appl. No. 12/122,603, Sep. 23, 2011, Office Action.
U.S. Appl. No. 12/393,877, Sep. 29, 2011, Office Action.
U.S. Appl. No. 11/427,297, Oct. 31, 2011, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/848,642, Nov. 9, 2012, Office Action.
U.S. Appl. No. 13/039,087, Nov. 6, 2012, Notice of Allowance.
U.S. Appl. No. 12/338,977, Nov. 28, 2012, Office Action.
U.S. Appl. No. 12/961,331, Dec. 4, 2012, Office Action.
U.S. Appl. No. 13/030,922, Dec. 18, 2012, Office Action.
U.S. Appl. No. 11/744,089, Aug. 8, 2012, Office Action.
U.S. Appl. No. 12/402,398, Sep. 20, 2012, Office Action.
U.S. Appl. No. 12/481,377, Aug. 10, 2012, Notice of Allowance.
U.S. Appl. No. 12/548,274, Sep. 10, 2012, Office Action.
U.S. Appl. No. 12/608,769, Aug. 22, 2012, Office Action.
U.S. Appl. No. 12/642,319, Aug. 28, 2012, Office Action.
U.S. Appl. No. 12/684,400, Oct. 16, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 12/684,562, Aug. 21, 2012, Office Action.
U.S. Appl. No. 12/684,569, Jul. 30, 2012, Office Action.
U.S. Appl. No. 12/688,065, Oct. 12, 2012, Office Action.
U.S. Appl. No. 12/848,642, Sep. 20, 2012, Restriction Requirement.
U.S. Appl. No. 12/850,242, Aug. 6, 2012, Restriction Requirement.
U.S. Appl. No. 12/850,242, Oct. 17, 2012, Office Action.
U.S. Appl. No. 12/955,859, Aug. 6, 2012, Office Action.
U.S. Appl. No. 12/987,792, Sep. 17, 2012, Office Action.
U.S. Appl. No. 11/344,891, Jun. 26, 2013, Issue Notification.
U.S. Appl. No. 12/402,398, Jun. 26, 2013, Issue Notification.
U.S. Appl. No. 13/112,631, Jun. 26, 2013, Office Action.
U.S. Appl. No. 11/427,309, Jun. 7, 2013, Notice of Allowance.
U.S. Appl. No. 13/112,618, Jun. 7, 2013, Office Action.
U.S. Appl. No. 13/488,233, Jun. 5, 2013, Issue Notification.
U.S. Appl. No. 10/908,721, Jul. 18, 2013, Notice of Allowance.
U.S. Appl. No. 11/744,089, Aug. 8, 2013, Notice of Allowance.
U.S. Appl. No. 12/850,242, Aug. 6, 2013, Notice of Allowance.
U.S. Appl. No. 12/955,859, Aug. 1, 2013, Notice of Allowance.
U.S. Appl. No. 13/615,547, Aug. 7, 2013, Issue Notification.
U.S. Appl. No. 12/338,977, Jul. 11, 2012, Office Action.
U.S. Appl. No. 13/039,087, Jul. 17, 2012, Office Action.
U.S. Appl. No. 12/106,928, Jun. 28, 2013, Office Action.
U.S. Appl. No. 12/106,937, Jun. 28, 2013, Office Action.
U.S. Appl. No. 12/941,809, Jul. 3, 2013, Office Action.
U.S. Appl. No. 12/961,331, Jul. 3, 2013, Office Action.
U.S. Appl. No. 13/153,594, May 29, 2013, Office Action.
U.S. Appl. No. 13/791,829, May 29, 2013, Office Action.
U.S. Appl. No. 13/898,202, filed May 20, 2013, Walberg et al.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 11/396,141, Apr. 30, 2013, Office Action.
U.S. Appl. No. 13/791,829, filed Mar. 8, 2013, Roorda et al.
U.S. Appl. No. 13/791,846, Mar. 8, 2013, Palermo.
U.S. Appl. No. 11/744,089, Apr. 15, 2013, Office Action.
U.S. Appl. No. 11/852,190, Apr. 24, 2013, Office Action.
U.S. Appl. No. 12/848,642, Apr. 26, 2013, Office Action.
U.S. Appl. No. 12/850,242, Apr. 18, 2013, Office Action.
U.S. Appl. No. 13/052,634, Feb. 8, 2013, Restriction Requirement.
U.S. Appl. No. 13/052,634, Apr. 22, 2013, Office Action.
U.S. Appl. No. 13/112,618, Mar. 29, 2013, Restriction Requirement.
U.S. Appl. No. 13/112,631, Mar. 29, 2013, Restriction Requirement.
U.S. Appl. No. 13/308,227, Apr. 10, 2013, Office Action.
U.S. Appl. No. 13/490,143, Apr. 29, 2013, Notice of Allowance.
U.S. Appl. No. 13/525,839, Apr. 1, 2013, Office Action.
U.S. Appl. No. 13/615,547, Apr. 12, 2013, Notice of Allowance.
U.S. Appl. No. 10/786,444, Jul. 11, 2013, Notice of Allowance.
U.S. Appl. No. 11/532,325, Jul. 17, 2013, Office Action.
U.S. Appl. No. 13/030,922, Jul. 18, 2013, Office Action.
U.S. Appl. No. 13/525,839, Jul. 15, 2013, Notice of Allowance.
U.S. Appl. No. 13/615,547, Jul. 10, 2013, Issue Notification.
U.S. Appl. No. 11/396,141, Aug. 21, 2013, Office Action.
U.S. Appl. No. 13/026,989, Aug. 23, 2013, Office Action.
U.S. Appl. No. 13/490,143, Aug. 21, 2013, Issue Notification.
U.S. Appl. No. 12/338,977, Jun. 19, 2013, Office Action.
U.S. Appl. No. 11/344,891, Jan. 22, 2013, Notice of Allowance.
U.S. Appl. No. 12/402,398, Mar. 13, 2013, Notice of Allowance.
U.S. Appl. No. 12/608,769, Feb. 27, 2013, Issue Notification.
U.S. Appl. No. 12/961,331, Feb. 1, 2013, Office Action.
U.S. Appl. No. 13/030,922, Jan. 31, 2013, Office Action.
U.S. Appl. No. 13/039,087, Feb. 27, 2013, Issue Notification.
U.S. Appl. No. 13/153,594, Jan. 29, 2013, Office Action.
U.S. Appl. No. 13/488,233, Feb. 5, 2013, Notice of Allowance.
U.S. Appl. No. 13/490,143, Jan. 4, 2013, Office Action.
U.S. Appl. No. 13/615,547, Jan. 18, 2013, Office Action.
U.S. Appl. No. 14/466,576, filed Aug. 22, 2014, Roorda et al.
U.S. Appl. No. 14/539,830, filed Nov. 12, 2014, Clark.
U.S. Appl. No. 11/455,993, Aug. 11, 2014, Notice of Allowance.
U.S. Appl. No. 11/958,295, Oct. 8, 2014, Issue Notification.
U.S. Appl. No. 11/958,295, Nov. 5, 2014, Issue Notification.
U.S. Appl. No. 12/106,928, Oct. 3, 2014, Notice of Allowance.
U.S. Appl. No. 12/113,851, Aug. 21, 2014, Office Action.
U.S. Appl. No. 12/393,877, Aug. 4, 2014, Notice of Allowance.
U.S. Appl. No. 12/403,277, Aug. 15, 2014, Office Action.
U.S. Appl. No. 12/548,274, Aug. 14, 2014, Office Action.
U.S. Appl. No. 12/642,319, Sep. 24, 2014, Issue Notification.
U.S. Appl. No. 12/684,562, Sep. 10, 2014, Office Action.
U.S. Appl. No. 12/987,792, Aug. 25, 2014, Notice of Allowance.
U.S. Appl. No. 13/222,899, Jul. 31, 2014, Office Action.
U.S. Appl. No. 13/898,202, Aug. 21, 2014, Office Action.
U.S. Appl. No. 14/246,926, filed Apr. 7, 2014, Carley et al.
U.S. Appl. No. 14/246,973, filed Apr. 1, 2014, Carley et al.
U.S. Appl. No. 14/323,753, filed Jul. 3, 2014, Fortson et al.
U.S. Appl. No. 11/113,549, Mar. 14, 2014, Notice of Allowance.
U.S. Appl. No. 11/113,549, Jul. 2, 2014, Issue Notification.
U.S. Appl. No. 11/396,141, Nov. 4, 2013, Notice of Allowance.
U.S. Appl. No. 11/411,925, Oct. 1, 2013, Office Action.
U.S. Appl. No. 11/411,925, Feb. 5, 2014, Notice of Allowance.
U.S. Appl. No. 11/411,925, Jun. 4, 2014, Issue Notification.
U.S. Appl. No. 11/455,993, Jan. 29, 2014, Office Action.
U.S. Appl. No. 11/532,325, Dec. 2, 2013, Office Action.
U.S. Appl. No. 11/674,930, Apr. 3, 2014, Notice of Allowance.
U.S. Appl. No. 11/674,930, Jul. 3, 2014, Notice of Allowance.
U.S. Appl. No. 11/852,190, Nov. 26, 2013, Office Action.
U.S. Appl. No. 11/852,190, Feb. 12, 2014, Notice of Allowance.
U.S. Appl. No. 11/852,190, Jun. 4, 2014, Issue Notification.
U.S. Appl. No. 11/958,295, Jun. 13, 2014, Notice of Allowance.
U.S. Appl. No. 12/106,928, Dec. 2, 2013, Office Action.

(56) References Cited

OTHER PUBLICATIONS

U.S. Appl. No. 12/106,928, Mar. 25, 2014, Advisory Action.
U.S. Appl. No. 12/106,937, Jan. 22, 2014, Office Action.
U.S. Appl. No. 12/113,851, Mar. 17, 2014, Office Action.
U.S. Appl. No. 12/114,031, Mar. 10, 2014, Office Action.
U.S. Appl. No. 12/122,603, Nov. 20, 2013, Office Action.
U.S. Appl. No. 12/122,603, Apr. 30, 2014, Office Action.
U.S. Appl. No. 12/403,277, Jan. 27, 2014, Office Action.
U.S. Appl. No. 12/642,319, Dec. 16, 2013, Office Action.
U.S. Appl. No. 12/642,319, May 27, 2014, Notice of Allowance.
U.S. Appl. No. 12/684,470, Jun. 4, 2014, Office Action.
U.S. Appl. No. 12/684,542, Jun. 18, 2014, Office Action.
U.S. Appl. No. 12/684,569, Apr. 23, 2014, Office Action.
U.S. Appl. No. 12/688,065, Oct. 18, 2013, Office Action.
U.S. Appl. No. 12/688,065, Apr. 8, 2014, Office Action.
U.S. Appl. No. 12/848,642, Feb. 3, 2014, Notice of Allowance.
U.S. Appl. No. 12/848,642, Jun. 4, 2014, Issue Notification.
U.S. Appl. No. 12/941,809, Nov. 8, 2013, Office Action.
U.S. Appl. No. 12/941,809, Feb. 3, 2014, Notice of Allowance.
U.S. Appl. No. 12/941,809, Jun. 4, 2014, Issue Notification.
U.S. Appl. No. 12/950,628, Apr. 25, 2014, Notice of Allowance.
U.S. Appl. No. 12/961,331, Sep. 20, 2013, Advisory Action.
U.S. Appl. No. 12/961,331, Apr. 25, 2014, Notice of Allowance.
U.S. Appl. No. 12/987,792, Jan. 21, 2014, Office Action.
U.S. Appl. No. 12/987,792, Jun. 11, 2014, Office Action.
U.S. Appl. No. 13/030,922, Jan. 8, 2014, Notice of Allowance.
U.S. Appl. No. 13/112,618, Nov. 20, 2013, Office Action.
U.S. Appl. No. 13/112,631, Dec. 2, 2013, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/308,227, Sep. 11, 2013, Office Action.
U.S. Appl. No. 13/791,829, Oct. 8, 2013, Notice of Allowance.
U.S. Appl. No. 13/898,202, Jan. 3, 2014, Office Action.
U.S. Appl. No. 14/562,467, filed Dec. 5, 2014, Ellingwood et al.
U.S. Appl. No. 11/396,731, Feb. 12, 2015, Office Action.
U.S. Appl. No. 11/532,325, Jan. 16, 2015, Notice of Allowance.
U.S. Appl. No. 12/106,937, Mar. 5, 2015, Notice of Allowance.
U.S. Appl. No. 12/113,851, Feb. 20, 2015, Notice of Allowance.
U.S. Appl. No. 12/114,091, Feb. 12, 2015, Office Action.
U.S. Appl. No. 12/684,400, Feb. 23, 2015, Office Action.
U.S. Appl. No. 12/684,470, Nov. 14, 2014, Office Action.
U.S. Appl. No. 12/684,542, Dec. 1, 2014, Office Action.
U.S. Appl. No. 12/684,562, Feb. 17, 2015, Notice of Allowance.
U.S. Appl. No. 13/112,618, Dec. 15, 2014, Office Action.
U.S. Appl. No. 13/112,631, Nov. 20, 2014, Office Action.
U.S. Appl. No. 13/898,202, Feb. 10, 2015, Notice of Allowance.
U.S. Appl. No. 14/017,039, Jan. 23, 2015, Office Action.
U.S. Appl. No. 12/122,603, Apr. 9, 2015, Office Action.
U.S. Appl. No. 13/112,631, Apr. 15, 2015, Office Action.
U.S. Appl. No. 13/222,899, Apr. 1, 2015, Office Action.
U.S. Appl. No. 14/732,977, Jun. 8, 2015, Walberg et al.
U.S. Appl No. 14/839,658, Aug. 31, 2015, Cummins et al.
U.S. Appl. No. 11/396,731, Jul. 9, 2015, Notice of Allowance.
U.S. Appl. No. 12/114,091, Jul. 23, 2015, Office Action.
U.S. Appl. No. 12/684,400, Jul. 28, 2015, Notice of Allowance.
U.S. Appl. No. 12/684,470, Aug. 26, 2015, Office Action.
U.S. Appl. No. 13/112,618, May 18, 2015, Office Action.
U.S. Appl. No. 13/222,899, Aug. 5, 2015, Office Action.
U.S. Appl. No. 13/308,227, Jul. 14, 2015, Office Action.
U.S. Appl. No. 13/791,846, Jun. 4, 2015, Office Action.
U.S. Appl. No. 13/908,796, Jul. 21, 2015, Office Action.
U.S. Appl. No. 14/017,039, Jun. 10, 2015, Office Action.
U.S. Appl. No. 14/023,428, Jul. 27, 2015, Office Action.
U.S. Appl. No. 14/077,007, Jul. 27, 2015, Office Action.
U.S. Appl. No. 14/246,926, Aug. 5, 2015, Office Action.
U.S. Appl. No. 14/246,973, Aug. 3, 2015, Office Action.
U.S. Appl. No. 14/466,576, Jul. 8, 2015, Office Action.

\* cited by examiner

CLOSURE DEVICE

CROSS REFERENCE

This application claims the benefit of, and priority to, U.S. Provisional Patent Application Ser. No. 61/109,822, filed on Oct. 30, 2008 and entitled "CLOSURE DEVICE," and Ser. No. 61/143,748, filed on Jan. 9, 2009 and entitled "CLOSURE DEVICE," both of which are incorporated in their entirety herein by this reference.

BACKGROUND

1. The Field of the Invention

The present disclosure relates generally to systems, devices, and methods for blocking an opening in body lumens. More particularly, the present disclosure relates to techniques for percutaneous closure of arterial and venous puncture sites, which are usually accessed through a tissue tract.

2. The Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique. Vascular access is generally provided through an introducer sheath, which is positioned to extend from outside the patient body into the vascular lumen. When vascular access is no longer required, the introducer sheath is removed and bleeding at the puncture site stopped.

One common approach for providing hemostasis (the cessation of bleeding) is to apply external force near and upstream from the puncture site, typically by manual compression. This approach suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, non-optical PTCA results, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may resulting in blood loss through the tract, hematoma and/or pseudo-aneurysm formation, as well as arteriovenous fistula formation. These complications may require blood transfusion and/or surgical intervention.

The incidence of complications from the manual compression procedure increases when the size of the introducer sheath grows larger, and/or when the patient is anticoagulated. The compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable sealing bodies is one example approach that has been proposed. Generally, this example approach relies on the placement of a thrombogenic and bioabsorbable material, such as collagen, at the superficial arterial wall over the puncture site. While potentially effective, this approach suffers from a number of problems. For example, bioabsorbable sealing bodies may lack a solid mechanical attachment of the sealing body to the tissue. Due to the lack of a solid mechanical attachment, the sealing body can wander within the tissue tract or move out of the puncture site, thus causing late bleeds. Conversely, if the sealing body wanders and intrudes too far into the arterial lumen, due to the lack of a solid mechanical attachment, intravascular clots and/or collagen pieces with thrombus attached can form and embolize downstream, causing vascular occlusion.

In addition to not having a solid mechanical attachment to the tissue, the sealing bodies may rely upon expandable materials to achieve hemostasis. Again, the expandable materials lack the security of a hard mechanical closure, thus potentially causing late bleeds and prolonging hemostasis.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments of the present invention provide systems, methods, and devices for closing an opening in tissue. Embodiments of the invention can be configured to close an opening within a body lumen.

In one example embodiment, a device for closing an opening in tissue includes a tubular body member having a wall thickness, a proximal end, and a distal end. The tubular body member of the device may include slits formed within the tubular member through the wall thickness. The slits are arranged above and below a waist portion located between the proximal end and distal end of the tubular body member.

In another example embodiment, a device for closing an opening in a body lumen wall includes a tubular body element having a first portion, a second portion, and a waist portion located between the first portion and second portion. The first and second portions have a delivery configuration and a deployed configuration. When the first and second portions are in the delivery configuration they have a delivery cross-sectional dimension, and when the first and second portions are in a deployed configuration they have a deployed cross-sectional dimension. The deployed cross-sectional dimension is larger than the delivery cross-sectional dimension.

Another example embodiment discloses a system for closing an opening in a body lumen. The system includes a closure element having a delivery configuration and a deployed configuration. The system further includes an actuator that is coupled to the closure element and operatively associated with a handle assembly. The handle assembly includes a rotatable handle element that may be inserted into a hub member such that when the handle element is rotated, the closure element changes from the delivery configuration to the deployed configuration.

In another example embodiment, a method for closing an opening in a body lumen is disclosed. The method includes inserting a closure device into an opening in a body lumen wall, the closure device including a closure element and actuator. After inserting the closure device, a force is applied to the closure element by way of the actuator such that a first portion of the closure element changes from a delivery configuration to a deployed configuration. Next, a second force may be applied to the closure element by way of the actuator such that a second portion of the closure element changes from a delivery configuration to a deployed configuration.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

In accordance with the present invention there is provided a closure device configured to close an opening formed in tissue. The closure devices described herein may be formed of a bioabsorbable material or may be formed of a biocompatible material. It is further contemplated the closure device may be coated with a covering membrane and/or another biocompatible coating as will be described in greater detail below. In one embodiment, the closure device may be configured to be received within the lumen of a medical sheath, for example, in accessing the patient's femoral artery, the physician will typically utilize a 6 French sheath. The closure device may be configured to be received within the lumen of this 6 French sheath. However, it can be understood that embodiments of the closure device may be configured to be received within multiple sizes of sheaths and should not be limited to the example above.

Figure 1:
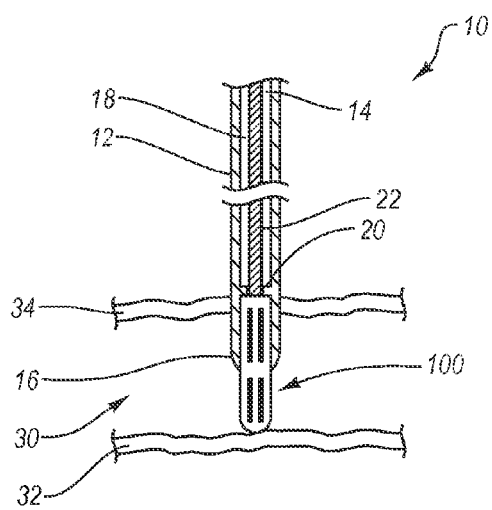
FIG. 1 is a cross-sectional view of the closure device in accordance with one embodiment of the present invention.

FIG. 1 illustrates one example embodiment of a closure device 10. As shown in FIG. 1 the closure device 10 may include an elongate member 12 that has a proximal end 14 and a distal end 16. The elongate member 12 may also include a passage 18 that extends from the proximal end 14 towards the distal end 16. Within the passage 18 of the elongate member 12, a protrusion 20 extends into the passage 18, thus reducing the cross-sectional dimension of the passage 18 at a location that is between the proximal end 14 and the distal end 16 of the elongate member 12. The closure device 10 further includes an actuator 22 that extends through the passage 18 of the elongate member 12. A closure element 100 extends beyond the elongate member 12 and may be coupled to the actuator 22.

Figure 2A:
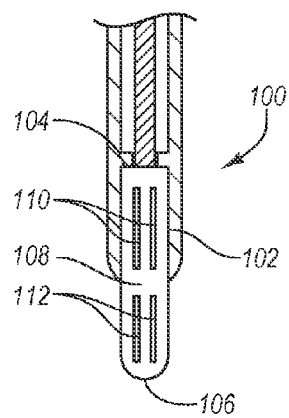
FIG. 2A is a close-up cross-sectional view of an example embodiment of a closure device in accordance with the present invention.
Figure 2B:
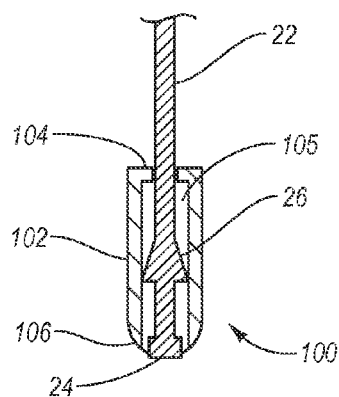
FIG. 2B is a close-up cross-sectional view of an example embodiment of a closure device in accordance with the present invention and further illustrating a locking mechanism formed therewith.
Figure 2C:
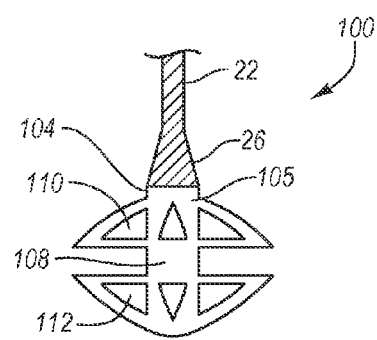
FIG. 2C is a cross-section view of an example embodiment of a closure element in a deployed configuration.

In operation, the closure device 10 may be inserted into a body lumen 30 as illustrated in FIG. 1. In one embodiment, the elongate member 12 and the closure element 100 pass through the proximal luminal wall 34 of the body lumen 30. While within the body lumen 30 the closure element 100 is changed from a delivery configuration, as illustrated in FIG. 1, to a deployed configuration as illustrated in FIG. 2C. While in the deployed configuration the closure element 100 is able to block or otherwise close a puncture in the proximal luminal wall 34.

Referring back to FIG. 1, the structure of the closure device 10 will be discussed in more detail. In particular, the closure device 10 may have configurations and characteristics that vary from one embodiment to the next. For example, the elongate member 12 is one aspect of the closure device 10 that may vary from one embodiment to the next. In particular, the elongate member 12 may have various geometric configurations. As illustrated in FIG. 1, the elongate member 12 may have a substantially circular cross-sectional geometric configuration. In other embodiments, however, the cross-sectional configuration of the elongate member 12 may vary and take various other configurations such as oval, square, triangular or any other configuration or combination of configurations.

Along with the various cross-sectional configurations of the elongate member 12, the passage 18 may also have various cross-sectional configurations. The cross-sectional configuration of the elongate member 12 may or may not match the cross-sectional configuration of the passage 18. Moreover, the cross-sectional configurations of the elongate member 12 and the passage 18 may vary from the proximal end to the distal end of the elongate member 12.

Notwithstanding variations in the geometric configuration, the elongate member 12 may be configured to retain the closure element 100 at the distal end 16 of the elongate member 12. In one example embodiment, illustrated in FIG. 1, the elongate member 12 further includes a protrusion 20 that protrudes inwardly into the passage 18 such that the closure element 100 is not permitted to pass the protrusion 20.

The protrusion 20, as illustrated in FIG. 1, also may include a passage such that the actuator 22 may pass through the protrusion section 20 and contact or couple to the closure element 100.

In one example, and as illustrated in FIG. 1, the closure element 100 is generally allowed to be inserted only about halfway into the passage 18 of the elongate member 12 and thereafter is blocked from being inserted further into the elongate member 12 by the protrusion 20. The location of the protrusion 20 may vary from one embodiment to the next. In other example embodiments, the protrusion 20 may be positioned more proximally within the passage 18 of the elongate member 12, or alternatively, the protrusion 20 may be positioned more distally within the elongate member 12. Thus, the position of the protrusion 20 may allow the closure element 100 to either be further inserted into the elongate member or have more of the closure element 100 positioned outside the elongate member 12.

In addition to variations of the protrusion 20 within the passage 18 of the elongate member 12, the distal end 16 of the elongate member 12 may also vary. For example and as illustrated in FIG. 1, the distal end 16 of the elongate member 12 may have a radius. This radius, for instance, may assist when inserting the elongate member 12 into a tissue tract and subsequently into the body lumen 30 through the proximal luminal wall 34. In other example embodiments, the distal end 16 of the elongate member 12 may have various other configurations. For example, they may have various ranges of radii as well as various other geometric configurations, for example, square, triangular, or rectangular.

In addition to the geometric configuration variations, the elongate member 12 may also have various material characteristics. For example, in one embodiment the elongate member 12 may be formed of a rigid material such as a stainless steel or other biocompatible material that is rigid. Alternatively, the elongate member 12 may be formed of a flexible material such as those materials utilized to form catheter shafts, introducer sheaths, or other medical devices. Suitable materials include polyvinyl chloride (PVC), peak, PTFE, nylon, or any other similar materials.

As discussed, the actuator 22 may extend through the elongate member 12. The actuator 22 is another aspect of the closure device 10 that may vary from one embodiment to the next. As shown in FIG. 1, the actuator 22 extends through the passage 18 of the elongate member 12 and couples to or attaches to the closure element 100. One way in which the actuator 22 may vary is the cross-sectional geometric configuration of the actuator. FIG. 1 illustrates an actuator 22 that has a substantially circular cross-sectional configuration. In other example embodiments, the cross-sectional geometric configuration of the actuator 22 may vary and include configurations such as square, triangular, rectangular or any other geometric configuration. In one example embodiment, the geometric configuration of the actuator 22 may be configured to match the cross-sectional geometric configuration of the passage 18 within the elongate member 12.

Another way in which the actuator 22 may vary is the material from which the actuator 22 is made. For example, the actuator 22 may be made from a rigid material such as stainless steel or other biocompatible materials that are rigid. Alternatively, the actuator 22 may be formed of a flexible material, for example, if the elongate member 12 is made from a flexible material. Examples of flexible actuator 22 materials include polyvinyl chloride (PVC), peak, PTFE, nylon, or similar materials. Generally, the actuator 22 material may be made from any material that is able to have enough strength and structural properties to change the closure element 100 from a delivery configuration, as shown in FIG. 2A, to a deployed configuration, as shown in FIG. 2C.

Another way in which the actuator 22 may vary is the way in which it connects to or attaches to the closure element 100. FIG. 2B illustrates a cross-sectional view of the closure element 100 that shows one example of connecting the actuator 22 to the closure element 100. For example, actuator 22 may include a coupler element 24 that is configured to couple to the distal end 106 of the closure element 100. In one example embodiment, and as illustrated in FIG. 2B, the coupler element 24 includes a section that has a larger cross-sectional dimension than the actuator 22. In this example, the coupler element 24 may interface with the distal end 106 of the closure element 100 such that the coupler element 24 is held by the material of the closure element 100 (e.g., the closure element 100 material surrounds the coupler element 24. In other example embodiments, the coupler element may simply attach to or couple to the distal end 106 of the closure element 100 by an adhesive or other bonding means.

In addition to the coupler element 24, the actuator 22 may also include a locking element 26, as illustrated in FIG. 2B. The locking element 26 may vary from one embodiment to the next. For example, and as illustrated in FIG. 2B, the locking element 26 has a triangular configuration, however, in other example embodiments the geometric configuration of the locking element may take various forms such as square, rectangular, oval, circular or any other configuration.

In particular, the geometric configuration of the locking element 26 is configured such that the locking element 26 and the proximal end 104 of the closure element 100 cooperate to lock the closure element 100 in the deployed configuration. For example, and as illustrated in FIGS. 2B and 2C, the locking element 26 may be pulled through the proximal end 104 of the closure element 100. Once pulled through the proximal end 104 of the closure element 100, the locking element 26 and/or the proximal end 104 of the closure element 100 may be configured such that the locking element 26, in combination with the proximal end 104 of the closure element 100, restricts the actuator from moving distally with respect to the closure element 100. In other words the locking element 26 may be configured to facilitate removal of the locking element 26 from within the closure element 100, but after removal from the closure element 100, the locking element 26 may not be allowed to re-enter the closure element 100.

Notwithstanding the various configurations and characteristics of both the elongate member 12 and the actuator 22, the closure element 100 may be configured to be operatively associated with the elongate member 12 and the actuator 22 in order to be delivered and deployed in an opening within a body lumen. Continuing now with FIGS. 2A, 2B, and 2C, the closure element 100 will be discussed in more detail. As illustrated in FIG. 2A, the closure element 100 may include a body member 102 that has a proximal end 104 and a distal end 106. The body member 102 may also include a waist portion 108 that separates a plurality of proximal slits 110 from a plurality of distal slits 112. Moreover, the closure element 100 may have a delivery configuration, as illustrated in FIG. 2A, and a deployed configuration, as illustrated in FIG. 2C.

As with other aspects of the closure device 10, the closure element 100 may vary from one embodiment to the next. One way in which the closure element 100 may vary is the cross-sectional configuration of the closure element 100 body member 102. For example, and as illustrated in FIG. 2A, the body member 102 may have a generally cylindrical cross-sectional configuration. In other example embodiments, the cross-sectional configuration of the body member 102 may take various forms such as square, rectangular, triangular or any other cross-sectional configuration.

Another way in which the closure element 100 may vary is the geometric dimensions of the proximal slits 110 and/or distal slits 112. For example, the geometric configuration of the upper and lower slits 110 and 112, as shown in FIG. 2A, may be a generally rectangular configuration. However, in other example embodiments the geometric configuration of the proximal slits 110 and/or the distal slits 112 may take various other geometric configurations such as more square, triangular, oval or any other configuration or combination configurations. The slits may be formed within the wall of the body member 102 using known manufacturing techniques such as cutting, laser cutting, water jet cutting. Alternatively, the slits may be integrally formed within the body member 102 during manufacturing such as through the use of injection molding.

Furthermore, and as illustrated in the example embodiment in FIG. 2A, the proximal slits 110 may have substantially the same configuration and dimensions as the distal slits 112. In other example embodiments, however, the proximal slits may have a different geometric configuration and/or dimension compared to the distal slits 112. For example, in one embodiment, the proximal slits 110 may have a different length and width as the distal slits 112, or the proximal slits 110 may have a different geometric configuration relative to the distal slits 112.

In addition to variations between the proximal slits 110 and the distal slits 112, the geometric configuration and the dimensions of the proximal slits 110 and/or distal slits 112 may vary from one slit to the next. For instance, the upper slits 110 may have a variety of different sized and configured slits that make up the plurality of upper slits 110. Similarly, the lower slits 112 may be made up of a variety of different sized and configured individual slits.

Another way in which the proximal slits 110 and distal slits 112 may vary is the alignment configuration between the proximal slits 110 with respect to the distal slits 112. For example, as illustrated in FIG. 2A, the proximal slits 110 may be substantially aligned with the distal slits 112. However, in other example embodiments, the proximal slits 110 may be positioned such that the proximal slits are misaligned with the distal slits 112. In the same respect, the number of proximal slits 110 compared to the number of distal slits 112 may vary from one embodiment to the next. As shown in FIG. 2A, there are an equal number of proximal slits 110 relative to the number of distal slits 112. In other examples, however, the closure element 100 may have more proximal slits 110 compared to distal slits 112. For example, a closure element may be configured such that there are six distal slits equally spaced around the body member 102 of the closure element 100, while there are only four proximal slits 110 positioned and equally spaced around the body member 102 of the closure element 100.

As can be understood, the spacing between each individual slit may also vary from one embodiment to the next, as well as from one slit to the next. For example, and as previously mentioned, the upper and/or lower slits 110 and 112 may have the slits positioned and equally spaced around the body member 102. Alternatively, the slits may be positioned around the body member 102 such that the spacing between slits varies.

The distance between the proximal slits 110 and the distal slits 112 is another aspect of the closure element 100 that may vary from one embodiment to the next. In one example embodiment, the distance between the proximal slits 110 and the distal slits 112 is a distance that would be approximately equal to the width of a body lumen wall. For example, the distance between the upper and distal slits may be equal to the width of the proximal lumen wall 34, illustrated in FIG. 1. In this manner, the closure element 100, when in the deployed configuration, would assist in blocking an opening within the proximal lumen wall 34.

FIG. 2B illustrates various other aspects of the closure element 100 that may vary from one embodiment to the next. For example, FIG. 2B illustrates that the closure element 100 may include an aperture 105 located on the proximal end 104 of the body member 102. In one embodiment, the proximal end 104 of the body member 102 of the closure element 100 may be made of material that is flexible such that the locking element 26 of the actuator may be pulled in a proximal direction through the aperture 105 located on the proximal end 104 of the closure element 100. Moreover, the proximal end 104 of the body member 102 may have a geometric and/or material configuration that allows the locking element 26 or similar feature of the actuator to pass through in one direction (i.e. the proximal direction) but not pass through in the opposite direction (i.e. the distal direction).

For example, the proximal end 104 may be configured with a plurality of cuts that are arranged in a generally circular pattern around the aperture 105 such that each cut extends away from the aperture along a radius line. The cuts may be formed at an angle such that the material on the proximal end 104 between the cuts are allowed to flex in a direction that would allow the locking element 26 to pass through the aperture 105 of the closure element 100. However, once the locking element 26 has passed through the aperture 105, the proximal end 104 material between the cuts is not permitted to flex to allow the locking element 26 to again pass through the aperture 105. In other words, the material at the proximal end 104 of the closure element 100 may only flex in one direction and thus resist movement of the locking element 26 in the distal direction after the locking element 26 has passed through the aperture 105.

The locking element 26, along with the configuration of the closure element 100 assist to change the closure element 100 from a delivery configuration, shown in FIGS. 1 and 2A, to a deployed configuration shown in FIG. 2C. In one embodiment, the actuator 22 cooperates with the closure element 100 to collapse the body member 102 of the closure element such that the proximal slits 110 and the distal slits 112 allow the portions of the body member 102 between the proximal slits 110 and distal slits 112 to collapse and flex radially outwardly. Moreover, when in the deployed configuration, the actuator 22, with the locking element 26 and the coupler element 24 may cooperate with the closure element 100 such that the body member 102 of the closure element 100 may be changed into, and held locked in, the deployed configuration. Specifically, the locking element 26 cooperates with the coupler element 24 such that the body member 102 of the closure element 100 is held in place in the deployed configuration between the locking element 26 and the coupler element 24.

The deployed configuration of the closure element 100 may have various configurations. For example, in one embodiment, the deployed configuration of the closure element 100 may provide a clamping force upon the body lumen wall, thus holding the closure element 100 in place within the opening in the body lumen. Additional characteristics and configurations of the closure element 100 in the deployed configuration will be discussed with respect to FIGS. 6 through 9B.

Another way in which the closure element 100 may vary is the type of material used to make the closure element 100. In one embodiment the closure element 100 is manufactured from a bioabsorbable, bioresorbable, bioerodible, and/or biodegradable material. Examples of suitable materials for use are metals, metal alloys, polymers or combinations thereof that decompose or biodegrade in a biological environment such as within a body lumen. For example, and not by limitation, suitable bioabsorbable materials may include magnesium, zinc, silicon, lithium, zinc titanium, magnesium lithium, polyglocic acid (PGA), polyhydroxybutyric acid, polyL-Lactic acid (PLLA), polydilactidel glycolide acid, polydilactid acid, PolyDL Lactide-co-gycolide, Polylactic acid, Polylicolic acid, Polyhydroxyalkanoates or derivatives thereof and any combination thereof.

In addition to the various types of materials that may be used to manufacture the closure element 100, the closure element 100 may include additional material properties that may be useful. For example, the closure element 100 may be covered with a flexible membrane to aid in sealing the opening. The flexible membrane may be formed of a flexible bio-compatible or bioabsorbable material such as any of those that were described above. Moreover, the closure element 100 may further include a beneficial agent either disposed thereon as a coating or integrally formed within the absorbable material wherein the beneficial agent would be configured to aid in healing and/or reduce the potential for infection.

Moreover, material properties may be included in the closure element 100 to help a user place the closure element 100. For example, the closure component 100 may further include a radiopaque marker or radiopaque coating in order to aid the user in positioning the closure element 100 within the puncture site of the body lumen. The radiopaque marker may be formed within the wall of the body member 102 in the form of a rivet. Alternatively, a radiopaque coating may be disposed on the body member 102 as a thin coating of radiopaque metal such as gold, tantalum, alydium, platinum, uridium or similar metals.

Referring now to FIGS. 3 through 6, the operation of the closure device 10 will be explained in more detail. Initially, the closure device 10 is inserted in a tissue tract and disposed through an opening or puncture within a body lumen. For example and as shown in FIG. 1, the closure device 10 may be disposed through the proximal lumen wall 34 of the body lumen 30. After disposing the closure device 10 through the opening in the proximal lumen wall 34 the closure element 100 may be changed from a delivery configuration to a deployed configuration.

In one embodiment, the process of changing the closure element 10 from a delivery configuration to a deployed configuration begins with positioning the closure element 100 within the elongate member 12 such that the distal slits 112 are located outside of the elongate member 12 and the proximal slits 110 are located within the elongate member 12. In one example, this position of the closure element 100 may correspond to the protrusion 20 located within the elongate member 12 as discussed above and as illustrated in FIG. 3.

Figure 3:
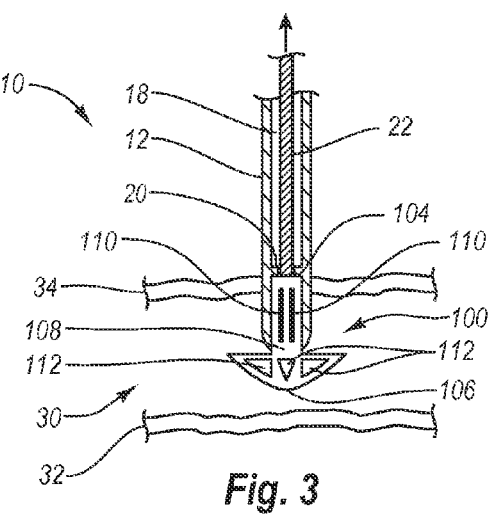
FIGS. 3 through 6 illustrate the use of an example closure device in accordance with the present invention.

With the distal slits 112 positioned outside of the elongate member 12, the actuator 22 may be moved in the proximal direction (as indicated by the arrow in FIG. 3) such that the portions of the body member 102 located in-between the distal slits 112 are forced to collapse, bend, and/or buckle and extend in an outward direction as shown in FIG. 3. In particular, the actuator 22 may pull the distal end 106 of the closure element 100 in a proximal direction by way of the coupler element 24 that is coupled to the distal end 106 of the closure element 100. The distal slits 112 may weaken the body member 102 such that upon experiencing the force associated with pulling the distal end 106 of the closure element 100 in the proximal direction, the portions of the body member 102 in-between the distal slits 112 collapse, the collapsing portions of the body member 102 extending out from the closure element 100. On the other hand, because the proximal slits 110 are positioned within and stabilized by the elongate member 12, the portions of the body member 102 in-between the proximal slits 110 may not collapse.

Figure 4:
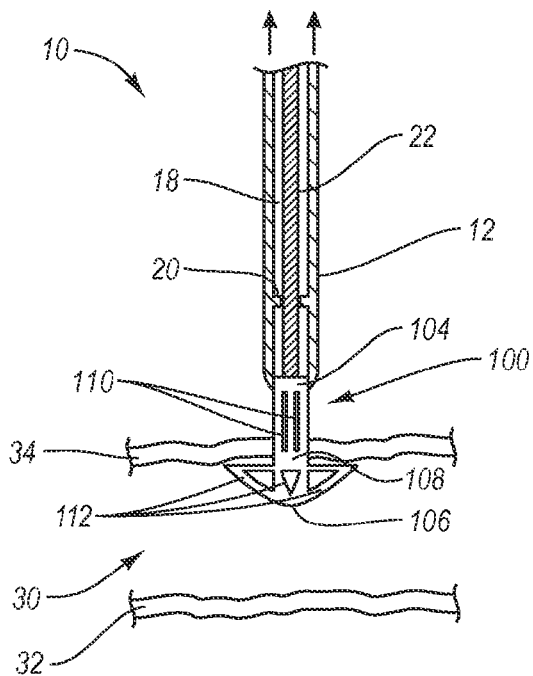

Once the portions of the body member 102 in-between the distal slits 112 have collapsed, the closure device 10 may be moved in the proximal direction such that the deployed lower section of the closure element 100 is generally in contact with the inside portion of the proximal lumen wall 34, as illustrated in FIG. 4. At this position, the deployed section of the closure element 100 is within the body lumen 30, the waist portion 108 of the closure element 100 extends through the opening in the proximal lumen wall 34, and the proximal slits 110 are located outside the body lumen 30.

When in this position, the elongate member 12 may be moved in a proximal direction relative to the closure element 100 such as to reveal or release the proximal slits 110 from the elongate member 12. In one example embodiment, the actuator 22 is held in substantially a constant position, while the elongate member 12 is pulled or otherwise moved in a proximal direction with respect to the closure element 100. Moreover, the distal end 16 of the elongate member 12 may be configured with a bias that applies a radially compressive force on the closure element 100. Thus, once the closure element is released from the elongate member 12, the user may sense the release and/or feel that the resistance to the movement of the elongate member 12 has changed indicating that the proximal slits 110 have been released from the elongate member 12.

Figure 5:
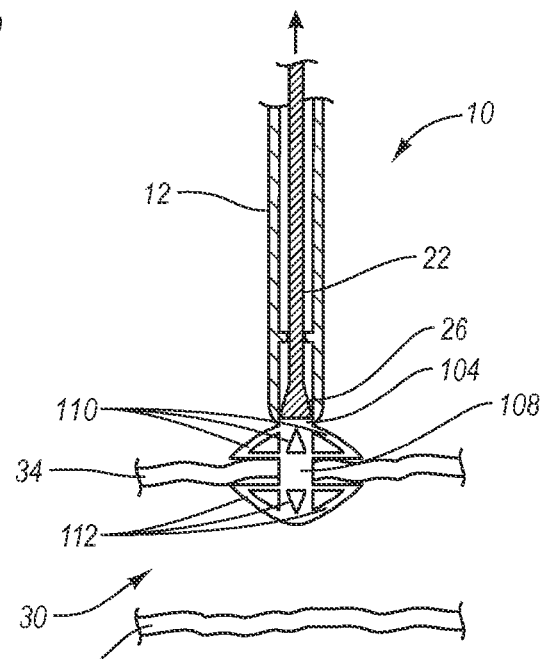

At this point the proximal slits 110 are now in position for the proximal portion of the closure element 100 to be deployed. As illustrated in FIG. 5, the proximal portion of the closure element 100 is deployed by having the portions of the body member 102 in-between the proximal slits 110 collapse such that the portions of the body member 102 in-between the proximal slits 110 extend radially outwardly as illustrated in FIG. 5. In order to deploy the upper portion of the closure element 100, the actuator 22 may be moved in a proximal direction (as illustrated by the arrow in FIG. 5) thus applying a force to the closure element 100 that causes the portions of the body member 102 in-between the proximal slits 110 to collapse and extend outwardly.

Moreover, and as illustrated in FIG. 5, during or after the deployment of the proximal portion of the closure element 100, the locking element 26 located on the actuator 22 may be pulled through the aperture 105 in the proximal end 104 of the closure element 100. The locking element 26 is then allowed to rest or push on the proximal end 104 of the closure element 100 such that the closure element is held in the deployed configuration between the locking element 26 and the coupler element 24 of the actuator.

Figure 6:
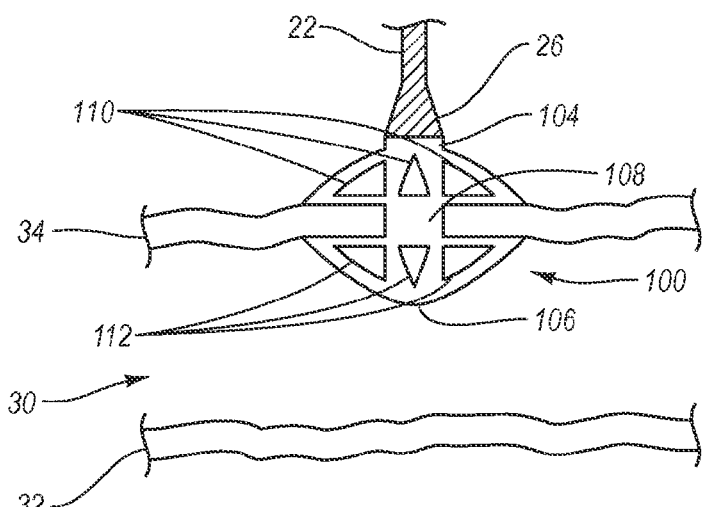

FIG. 6 shows a close-up view of a deployed closure element 100 within an opening of a body lumen 30. As shown in FIG. 6, the proximal slits 110 and distal slits 112 have allowed the proximal and distal portions of the body member 102 to collapse, and thus the portions of the body member 102 in-between the slits have extended outwardly such that the proximal lumen wall 34 is located between the collapsed proximal portion and the collapsed distal portion of the closure element 100. The waist portion 108 of the body member 102 may be located at least partially within the opening in the proximal lumen wall 34 of the body lumen 30.

FIG. 6 further illustrates that the deployed closure element 100 may be held in a deployed configuration by the coupler element 24 and the locking element 26. In particular, the locking element 26 cooperates with the coupler element 24 such that the closure element 100 is squeezed or otherwise restricted between the coupler element 24 and the locking element 26. In this way, the portions of the body member 102 that have collapsed are held in the collapsed or deployed configuration and are not permitted to return to the pre-collapsed or delivery configuration.

Once the closure element 100 is locked in the deployed configuration, the actuator 22 portion proximal to the locking element 26 may be severed or cut using a secondary cutting device or, alternatively, the actuator 22 may be configured such that upon application of another proximal force a weakened portion of the actuator 22 allows the actuator to break free at a location on the actuator 22 that is proximal to the locking element 26. The severed actuator 22 and the elongate member 12 are then removed from the tissue tract leaving the deployed closure element 100 within the puncture or opening within the body lumen 30.

Figure 7A:
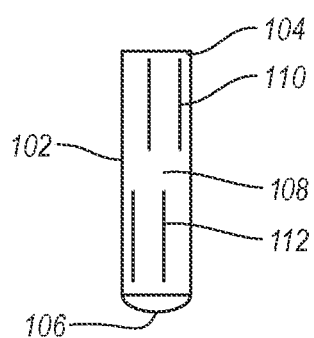
FIGS. 7A through 9B illustrate various embodiments of a closure element in accordance with the present invention.

FIGS. 7A through 8B illustrate various additional example embodiments of the closure element 100. For example, FIG. 7A illustrates a closure element 100 that includes a body member 102 with a proximal end 104 and a distal end 106. The body member 102 has proximal slits 110 and distal slits 112 formed within the body member 102 of the closure element 100. The proximal slits 110 and the distal slits 112 may have various arrangements and alignments with respect to one another. The arrangement and alignment of the proximal slits 110 and the distal slits 112 may affect the deployed configuration of the closure element 100. Thus, the proximal slits 110 and the distal slits 112 may have almost any arrangement and alignment configurations that subsequently determine the deployed configuration of the closure element 100.

Figure 7B:
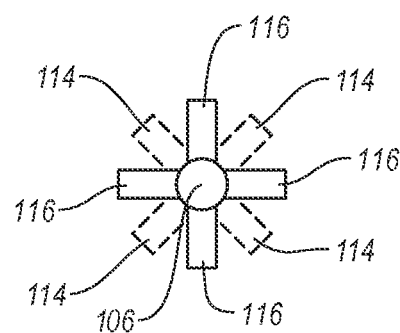

For example, and as illustrated in FIGS. 7A through 7B, the closure element 100 may take various forms. In particular, the example closure element 100, illustrated in FIG. 7A, includes proximal slits 110 that are offset from the distal slits 112. In other words, the proximal slits 110 are not vertically aligned with the distal slits 112. This example offset arrangement of the proximal and distal slits 110 and 112 may result in the closure element 100 having a deployed configuration as illustrated in FIG. 7B.

Specifically, when in the deployed configuration, the closure element 100 has upper extensions 114 and lower extensions 116. As illustrated in FIG. 7B, the upper extensions 114 may be offset from the lower extensions 116 such that the upper extensions 114 and lower extensions 116 alternate as viewed from the distal end 106 of the closure element 100. In other example embodiments, the upper extensions 114 and lower extensions 116 may be configured such to have any pattern of alignment or arrangement with respect to one another or with respect to other portions of the closure element 100 depending on the alignment or arrangement of the proximal slits 110 with respect to the distal slits 112.

Figure 8A:
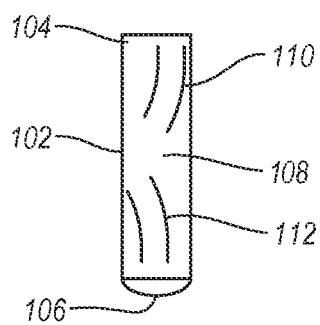
Figure 8B:
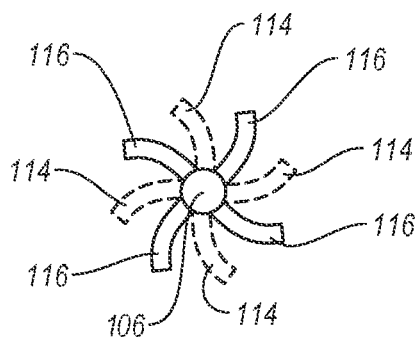

FIG. 8A shows another alternative embodiment of the closure element 100 that varies the configuration of the proximal slits 110 and the lower slits 112 to produce another example of the deployed configuration of the closure element 100. As illustrated in FIG. 8A, the closure element 100 has a body member 102 that has a proximal end 104 and distal end 106 and also includes a waist portion 108. The waist portion 108 is positioned between proximal slits 110 and distal slits 112. In this example embodiment, the proximal and distal slits 110 and 112 are curved or have a radius, as illustrated in FIG. 8A. The curved proximal slits 110 and curved distal slits 112 produce curved upper and lower extensions 114 and 116 when the closure element 100 is changed into the deployed configuration. Moreover, and as illustrated in FIG. 8B, the curved upper and lower extensions 114 and 116 may alternate one from another. As with the embodiment shown in FIG. 7A, the curved upper and lower extensions 114 and 116 may have any alignment or arrangement configuration with respect to one another.

In addition to the two embodiments of the closure element 100, illustrated in FIG. 7A through FIG. 8B, the upper and distal slits 110 and 112 may have various other configurations such as a zigzag pattern, an oval pattern or any other pattern or configuration that would produce various arrangement and alignment configurations of the upper extensions 114 and/or lower extensions 116. Moreover, there can be any combination between the proximal slits 110 and the distal slits 112. For example, the proximal slits may take on a more rectangular configuration, as shown in FIG. 7A, and the distal slits 112 may take on a curved configuration as shown in 8A. Thus, the deployed configuration of the closure element 100 may have upper extensions 114 that are rectangular, as shown in 7B, and lower extensions 116 that are curved, as shown in FIG. 8B.

Figure 9A:
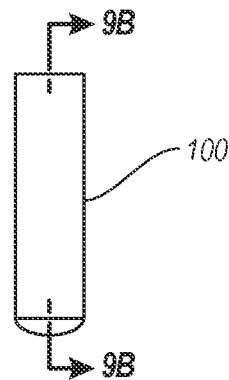
Figure 9B:
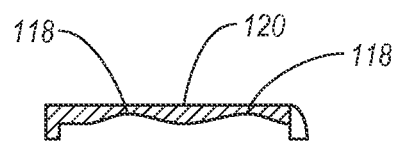

Although FIGS. 7A through 8B addresses various example configurations of the closure element 100 that have proximal and distal slits 110 and 112, the closure element 100 may be configured to not contain any slits. For example, FIGS. 9A and 9B show an example embodiment of a closure element 100 that does not include any proximal or distal slits; however, the closure element 100 is still able to collapse such to form the deployed configuration of the closure element 100. In particular, the sidewall of the closure element 100, as illustrated in FIG. 9B, may include indentations 118 or other areas within the wall that create natural weaknesses or breaking points. The indentations 118 within the closure element wall 120 may be configured such that when a compressive force is applied from the actuator 22, the closure element 100 collapses around the weakened portions of the indentation 118.

The indentations 118, shown in FIG. 9B, may vary from one embodiment to the next. For example, the number of indentations that are located on the sidewall 120 of the closure element 100 may vary. In one example embodiment illustrated in FIG. 9B, the sidewall 120 of the closure element 100 includes two indentations 118. Each indentation 118 would produce extensions when the closure device is changed to the deployed configuration, thus two extensions (for example an upper and lower extension) would be made from the example embodiment shown in FIG. 9B. However, in other example embodiments, more or less indentations may be used in order to create various or multiple sections of that collapse to form a barrier within an opening of a body lumen.

Figure 10:
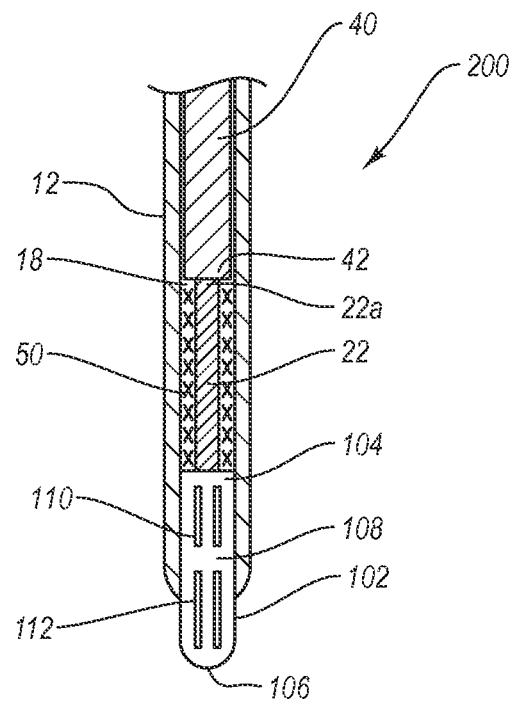
FIGS. 10 and 11 are cross-sectional views of an alternative embodiment of a closure device including a charge of a hemostatic material.
Figure 11:
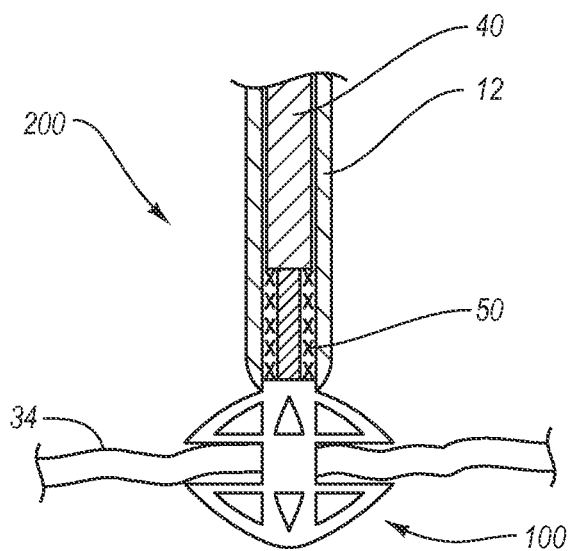

FIGS. 10 and 11 show another optional embodiment of a closure device 200. As illustrated in FIG. 10, closure device 200 may include an elongate member 12 that has a passage 18 extending through from a proximal end to a distal end. The elongate member 12 may be configured to accept and retain a closure element 100. The closure element may include a proximal end 104, a distal end 106, and a waist portion 108 that is located between the proximal end 104 and the distal end 106. In one embodiment, the closure element 100 may contain proximal slits 110 and distal slits 112, as previously discussed. Closure device 200 further includes an actuator 22 that is connected to the closure element 100. The actuator 22 is associated with a second actuator 40. Located within the passage 18 within the elongate member 12 may be a hemostatic agent 50.

In one example embodiment of the closure device 200, the second actuator 40 has a slightly larger cross-sectional dimension than the cross-sectional dimension of the actuator 22. In this way a space is located in the passage 18 between the elongate member 12 and the actuator 22 such that a hemostatic agent 50 may be placed next to the actuator 22. Moreover, the second actuator 40 may be configured and sized appropriately such that the clearance between the second actuator 40 and the elongate member 12 through the passage 18 is minimal, allowing the second actuator 40 to press or move the hemostatic agent 50 through the passage 18 of the elongate member 12.

As shown in FIG. 11, the basic operation of the closure device 200 may be similar to the basic operation previously discussed with closure device 10. However, in this embodiment after the closure element 100 is secured in the deployed configuration about the proximal lumen wall 34, the second actuator 40 will then be positioned to press the hemostatic agent 50 out of the elongate member 12. Specifically, once the closure element 100 is in the deployed configuration, the elongate member 12 may be moved in the proximal direction and the second actuator 40 may be pressed in the distal direction such that the hemostatic agent 50 is forced out of the elongate member 12 and onto the surface of the deployed closure element 100, and thus the hemostatic agent may be deposited onto the portion of the proximal lumen wall 34 that is in the general area of the deployed closure element 100.

The hemostatic agent 50 may be any material configured to aid in the healing of the body lumen wall as well as to cause the cessation of bleeding. Moreover, the hemostatic agent 50 may contain any material or agent that may be used to avoid infection. Suitable hemostatic materials for any of the embodiments described above may include chitosan, collagen, thrombin, PEG or other biocompatible materials. In one embodiment, chitosan may be utilized. The chitosan hemostatic composition may provide a strong clotting action to seal a hole, puncture, incision, or any other bleeding site to promote enhanced healing of the bleeding site and reduce opportunities for infection. Additionally, the chitosan hemostatic composition can be configured to swell in the presence of blood to form a hemostatic barrier that covers or otherwise plugs the bleeding site.

Chitosan is a polycationic polymer derived from chitin, which can also be used as described herein. Chitosan has a positive charge from primary amine groups that can interact with the negative charge of the lipids present on cell surfaces, such as blood cells. This electrostatic interaction has been identified as an aspect of the hemostatic properties of chitosan. Dry chitosan compositions can have increased hemostatic properties by increasing surface area, and thereby the contact area with blood. Processing methods, such as freeze drying, puffing, foaming, sponging, ballooning, combinations thereof, or the like, can be used to provide a porous, open cellular, or closed cellular structure with increased surface area. In addition to chitosan and/or chitin, other polymers having N-acetylglucosamines and N-glucosamines, such as poly-beta-1→4-N-acetylglucosamines with or without one or more monosaccharides being deacetylated and poly-beta-1→4-N-glucosamines, and derivatives thereof.

The chitosan or other similar polymer used in various embodiments of the present invention may be purified to facilitate use in a medical device and or used within the body of a subject. This may include being purified to remove proteins, other organic or inorganic contaminants. Such purification and processing of chitosan is well known in the art. Accordingly, the chitosan or other similar polymer can be considered to be biocompatible, immunoneutral, and/or generally recognized as safe for use with or within a subject, such as a human or other animal.

Once the hemostatic agent 50 has been deployed next to the deployed closure element 100, the elongate member 12 along with the associated actuator 22 and second actuator 40 may be removed from the patient.

The closure device discussed with the various example embodiments of the present invention may include various other configurations. For example, any configuration of the closure device that includes a closure element that is able to anchor on the inside surface of the body lumen wall as well as on the outside surface of the body lumen wall (i.e. sandwich the wall of the body lumen between two closure elements or two closure element portions) may be used with the closure device contemplated with the present invention.

Figure 12:
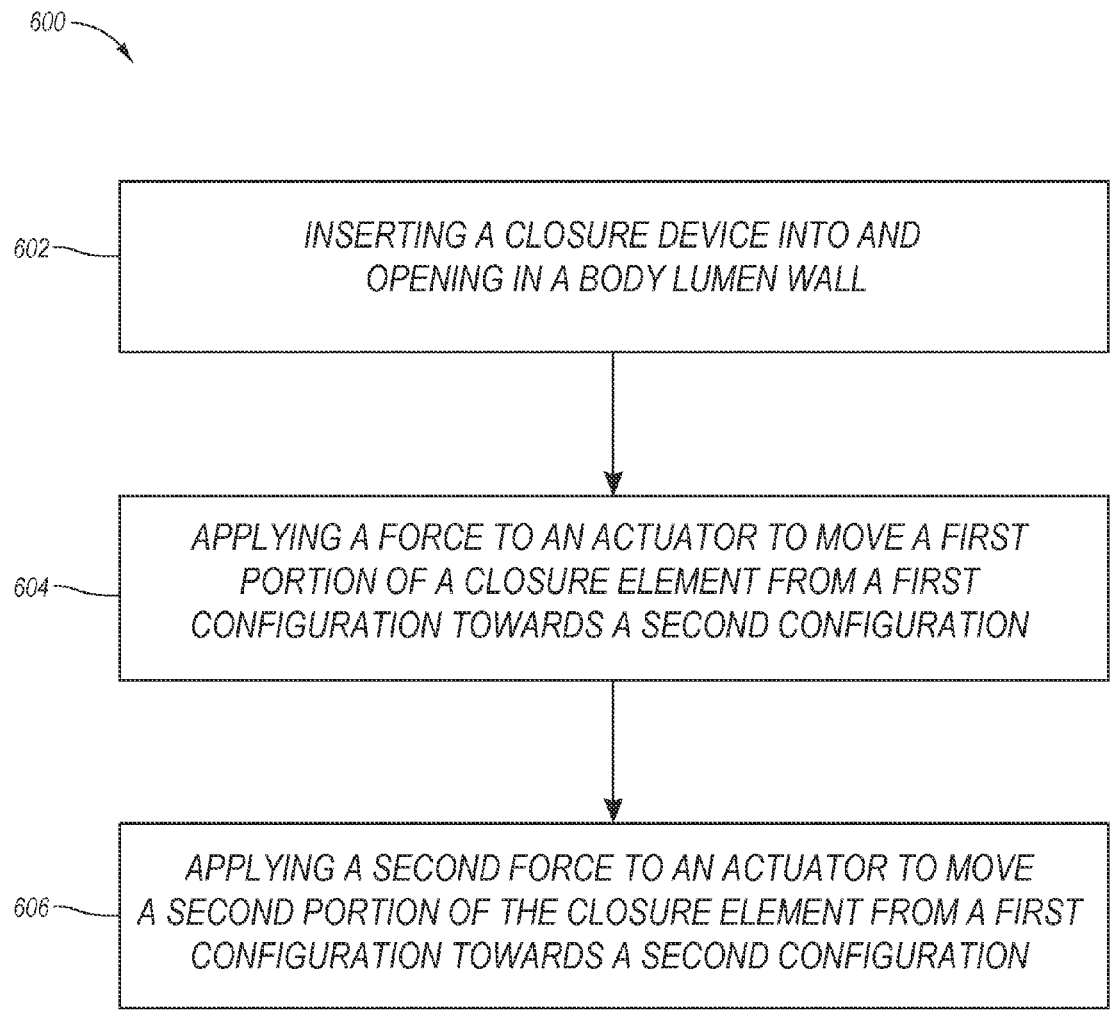
FIG. 12 is a flow chart showing an example method of closing an opening in tissue in accordance with the present invention.

Accordingly, the previous figures and the corresponding text provide a number of different components and systems that may be used to close an opening in a body lumen. In addition to the foregoing, other example embodiments may also be described in terms of flowcharts comprising one or more acts in a method for accomplishing a particular result. For example, FIG. 12 illustrates a method 600 of closing an opening in tissue. The acts of method 600 are discussed more fully below with respect to the disclosures of FIGS. 1 through 11.

For example, FIG. 12 shows that a method in accordance with an example implementation of the invention may include inserting 602 a closure device into an opening in a body lumen wall. Inserting a closure device may involve inserting a closure device into an opening formed in tissue, the closure device including a delivery tube, an actuator, and a closure element, the closure element defined by a body having a proximal portion, a distal portion and a waist. For example, as shown in FIG. 3, the closure element 100 may be inserted through the proximal lumen wall 34.

After the closure device is inserted into an opening, a force may be applied 604 to the actuator to move a first portion of a closure element from a first configuration to a second configuration. Applying a force may involve applying a force to the actuator to move the distal portion of the closure element from a first configuration toward a second configuration, wherein in the second configuration, portions of the closure element protrude from the body. For example, as shown in FIG. 3, the actuator 22 may be moved in a proximal direction (as indicated by the arrow) such that the portions of the body member 102 located in-between the distal slits 112 are forced to collapse, bend, and/or buckle and extend in an outward direction thus causing the distal portion of the closure element 100 to change from a delivery configuration to a deployed configuration.

Next, a second force may be applied 606 to an actuator to move a second portion of the closure element from a first configuration towards a second configuration. Applying a second force may involve applying a second force to the actuator to move the proximal portion of the closure element from a first configuration toward a second configuration. For example, and as illustrated in FIG. 5, the actuator 22 may be moved in a proximal direction, thus causing the portions of the body member 102 in-between the proximal slits 110 to collapse and extend outwardly.

Figures 13A, 13B:
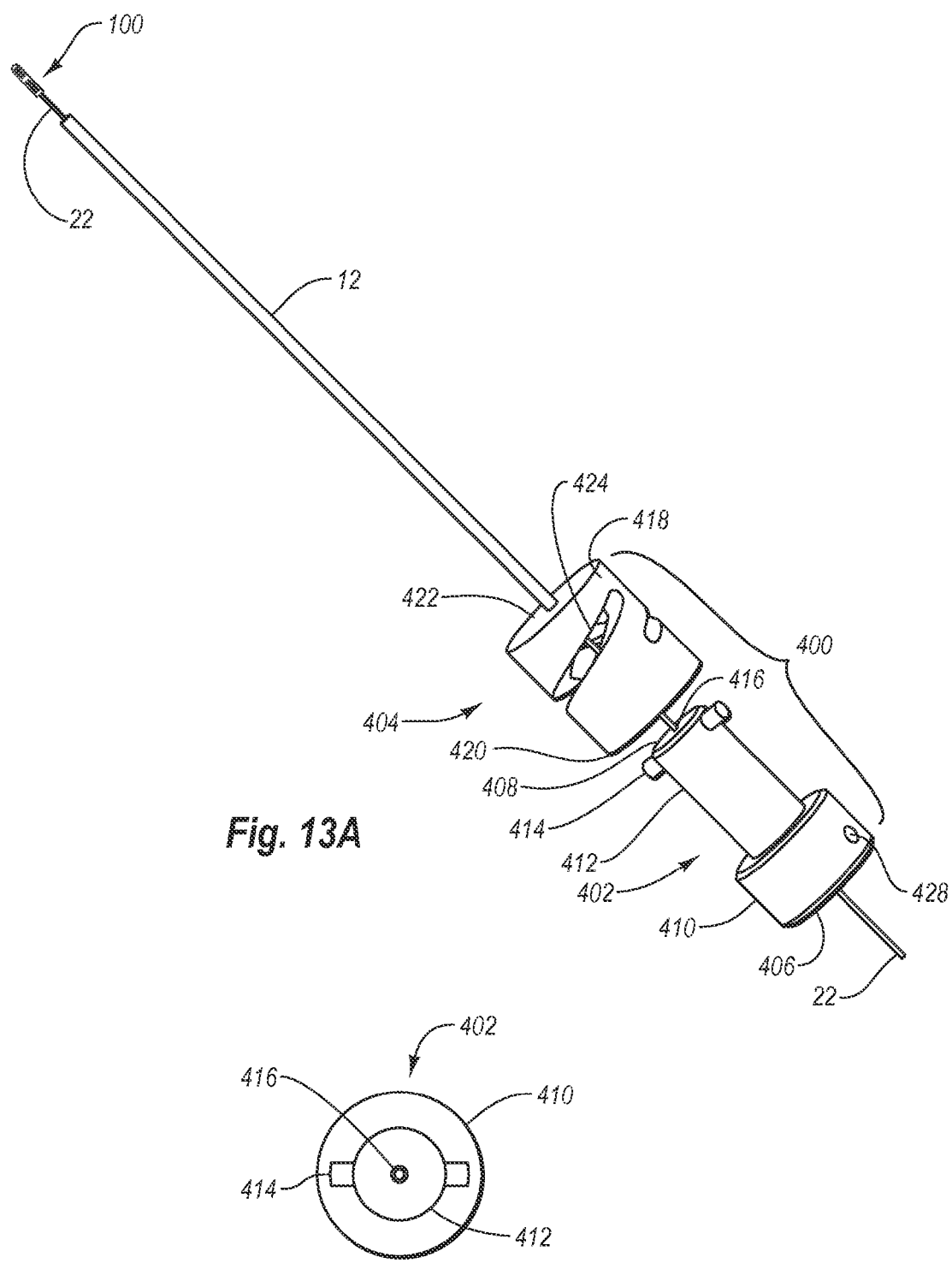
FIG. 13A is an exploded illustration of a delivery system of one embodiment of the present invention.
FIG. 13B is a top view of a portion of the delivery system of FIG. 13A according to one embodiment of the present invention.

FIGS. 13A through 13G illustrate an example embodiment of a closure device that uses a handle assembly 400. In particular, FIG. 13A illustrates a closure device that includes a handle assembly 400 that has a handle element 402 and a hub member 404. The handle element 402 has a proximal end 406, a distal end 408, a grip portion 410, and an extended portion 412. Projections 414 may extend from the extended portion 412. Moreover, the handle element 402 includes a port 416 through which an actuator 22 may extend.

The handle element 402 is operatively associated with a hub member 404. The hub member 404 includes a hub body 418 that has a proximal end 420 and a distal end 422. A channel 424 is formed within the hub body 418 of the hub member 404, the channel 424 configured to cooperate with the projections 414 located on the handle element 402. An elongate member 12 may be connected to the hub member 404. The elongate member 12 may be configured such that an actuator 22 may extend through the elongate member 12. Attached to a distal end of the actuator 22 is a closure element 100, as illustrated in FIG. 13A.

Briefly, in operation, the handle assembly 400 assists a user in deploying the closure element 100 within an opening in a body lumen. For example, after the closure element 100 is positioned appropriately within the opening in the body lumen, as discussed above, the user may turn the handle element 402, which in turn assists to deploy the closure element 100. Specifically, the handle element 402 may be coupled to the actuator 22 such that as the handle element 402 is rotated, the actuator applies a force upon the closure element 100 that causes the closure element 100 to change from a delivery configuration to a deployed configuration, as discussed above.

The handle assembly 400, shown in FIG. 13A, may vary from one embodiment to the next. For example, the handle element 402 is one example aspect of the handle assembly 400 that may vary. FIG. 13B shows a bottom view of the handle element 402. The bottom view of the handle element 402 illustrates the grip portion 410, the extended portion 412, and the projections 414 that extend from or project out from the extended portion 412. Moreover, FIG. 13B illustrates the port 416 through which the actuator 22 may extend.

The geometric configuration is one way in which the handle element 402 may vary. As illustrated in FIG. 13B, the geometric configuration of the handle element 402 may have a substantially circular cross-sectional configuration. However, in other example embodiments, the cross-sectional configuration of the handle element including the extended portion 412 and the grip portion 410 may have various other geometric configurations such as square, rectangle, triangle or any other configuration or combination of configurations.

Figures 13C, 13D:
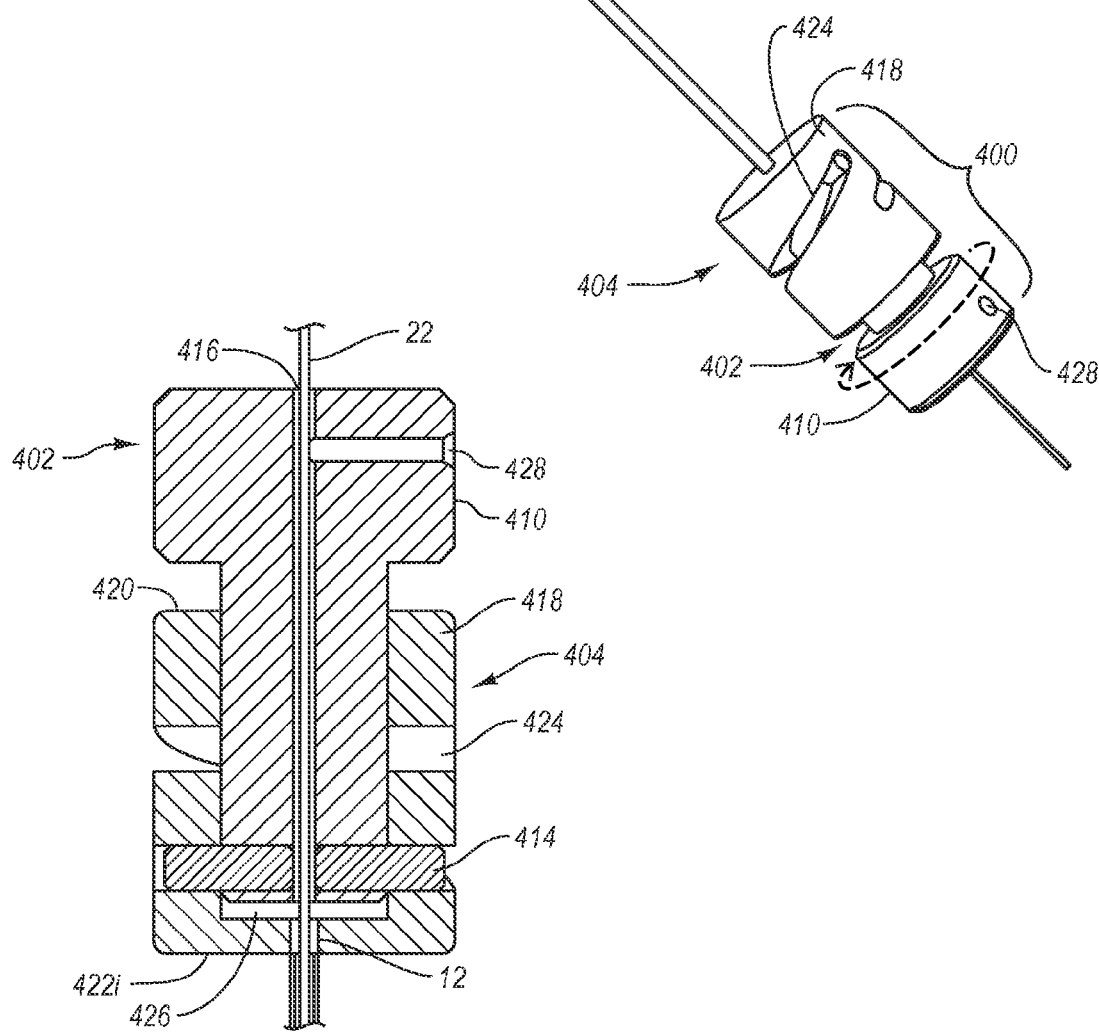
FIG. 13C is another illustration of the delivery system of FIG. 13A according to one embodiment of the present invention.
FIG. 13D is a cross-section illustration of a portion of the delivery system of FIG. 13A.

Moreover, and as shown in FIGS. 13A and 13D, the handle element 402 may include a set screw 428. The set screw 428 may be positioned in the grip portion 410 such that a set screw may be used to secure the position of the actuator 22. FIG. 13D illustrates how the set screw 428 may be positioned such to enter from the side of the grip portion 410 and into the port 416, and thus, secure the actuator 22.

Another way in which the handle element 402 may vary is the characteristics of the projections 414. As shown in FIG. 13D, the projections 414 may be made from a different piece of material than the extended portion 412. In alternate embodiments, the projections 414 may be manufactured out of the same piece of material as the extended portion 412.

Not only can the manufacture method vary with respect to the projections 414, but the location of the projections 414 on the extended portion 412 may vary from one embodiment to the next. As illustrated in FIGS. 13A and 13D, the projections 414 may be located on the distal end 408 of the handle element 402. However, in alternative embodiments, the projections 414 may be located at various other locations or almost any location on the extended portion 412.

Another aspect of the handle element 402 that may vary from one embodiment to the next is the grip portion 410. The grip portion 410 may be sized such that a human finger or a human hand would be able to easily turn and twist the grip portion 410. In order to help with the twisting of the handle element 402, the grip portion 410 may include a friction provider such as a piece of rubber or a pattern within the sidewall of the grip portion to aid in helping a human hand grip the grip portion 410 and turn the handle element 402.

In addition to various geometric characteristics, the handle element 402 may vary in material composition. For example, in one example embodiment the handle element 402 may be made from a metal such as stainless steel. Other materials may be used to make the handle element 402 such as plastics, ceramics or any other material that would have structurally suitable properties.

Just as the handle element 402 may vary from one embodiment to the next, so too may the hub member 404. For example, the cross-sectional configuration of the hub member 404 may vary from one embodiment to the next. The hub member, as illustrated in FIG. 13A, has a substantially circular cross-sectional geometric configuration. Alternatively, in other example embodiments, the hub member 404 may have a cross-sectional geometric configuration that is square, rectangular, hexagonal, or any other configuration or combination of configurations.

Notwithstanding the cross-sectional configuration of the hub member 404, the way in which the channel 424 is located throughout the hub member 404 may vary. For example, and as illustrated in FIG. 13A, the channel 424 is configured such that the handle element 402 is allowed to rotate one full turn within the hub member 404. Alternatively, the channel 424 may be configured to allow more or less rotation of the handle element 402. In one example embodiment, the channel 424 may only allow for a half turn of the handle element 402. Alternatively, in other embodiments of the invention, the channel 424 may allow for multiple rotations of the handle element 402.

In addition to the number of rotations in which the channel 424 allows the handle element 402 to make, the channel 424 may also be configured with various pathways. For example, and as illustrated in FIG. 13A, the pathway of the channel 424 is relatively smooth from the bottom portion of the channel 424 around to the top portion of the channel 424. However, in alternative embodiments, the channel 424 may have step sections such that the projections 414 on the handle element 402 move within the channel at various steps from one depth to the next. In another example embodiment, the channel 424 may direct the handle element 402 to move with a combination of relatively smooth movements and stepped movements.

The operation of the handle assembly 400 will be discussed in further detail with reference to FIGS. 13C through 13G. The handle element 402 is inserted within a receiving area 426 located within the hub member 404, as illustrated in FIG. 13D. The projections 414 located on the extended portion 412 of the handle element 402 interact with the channel 424 on the hub member 404 such that as the handle element 402 is turned, the position of the handle element relative to the hub member 404 changes.

For example, and as illustrated in FIG. 13C, the handle element 402 is located towards the distal end of the hub member 404. When the handle element 402 is rotated, the projections 414 follow the channels 424 such that the handle element 402 moves in the proximal direction with respect to the hub member 404, as illustrated in more detail in FIGS. 13E and 13F. Moreover, if the actuator 22 is secured to the handle element 402 by way of the set screw 428, then as the handle element 402 moves in the proximal direction with respect to hub member 404, the handle element 402 also pulls the actuator 22 in the proximal direction. Thus, as the handle element 402 is rotated, the actuator 22 is pulled in a proximal direction and the closure element 100 may be deployed, as previously described with relation to FIGS. 3 through 6.

Figure 13E:
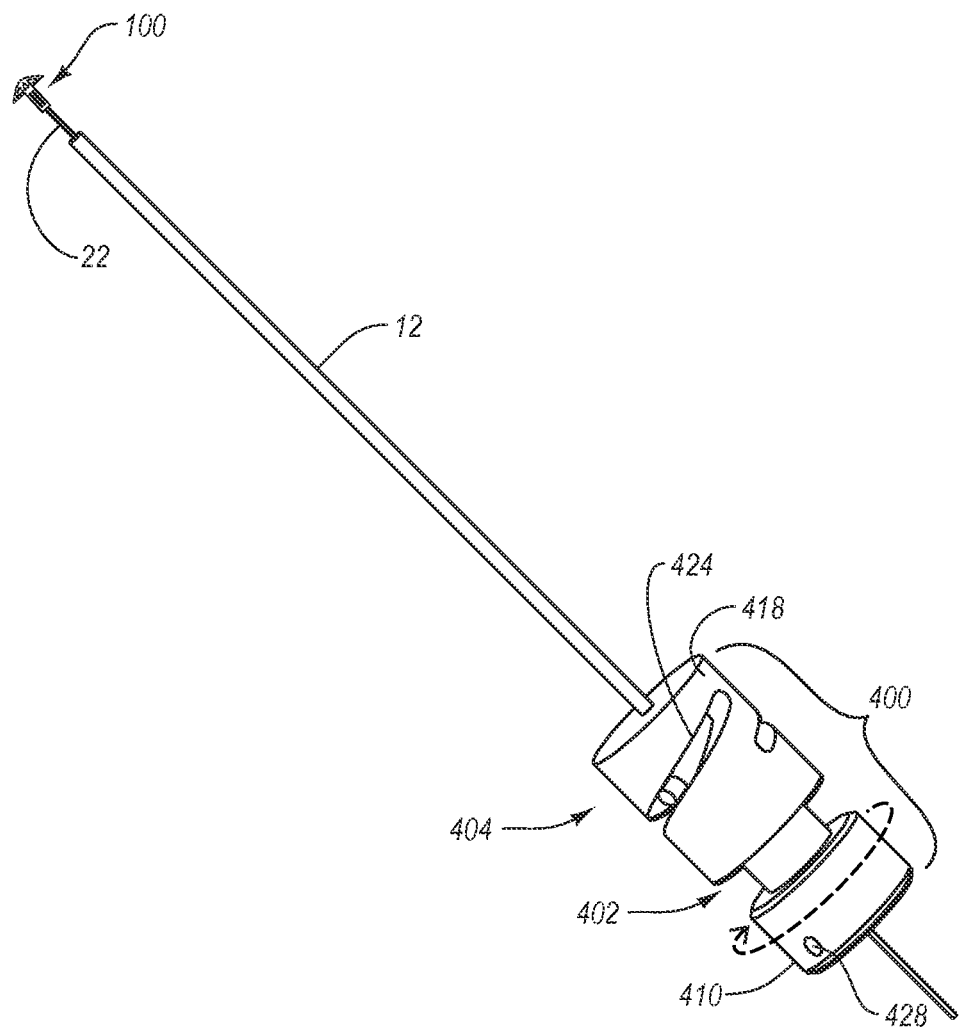
FIG. 13E is a further illustration of the delivery system of FIG. 13A.
Figure 13F:
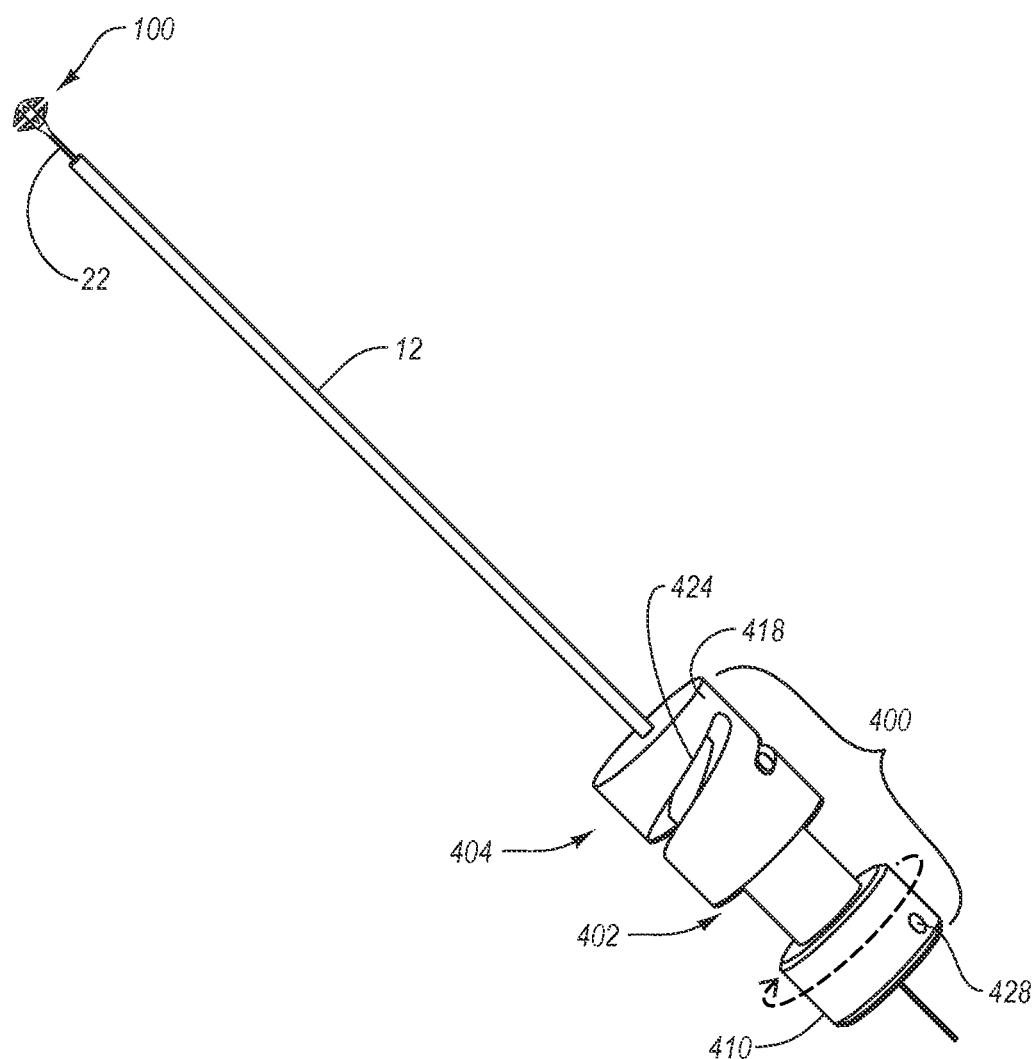
FIG. 13F is a yet further illustration of the delivery system of FIG. 13A.
Figure 13G:
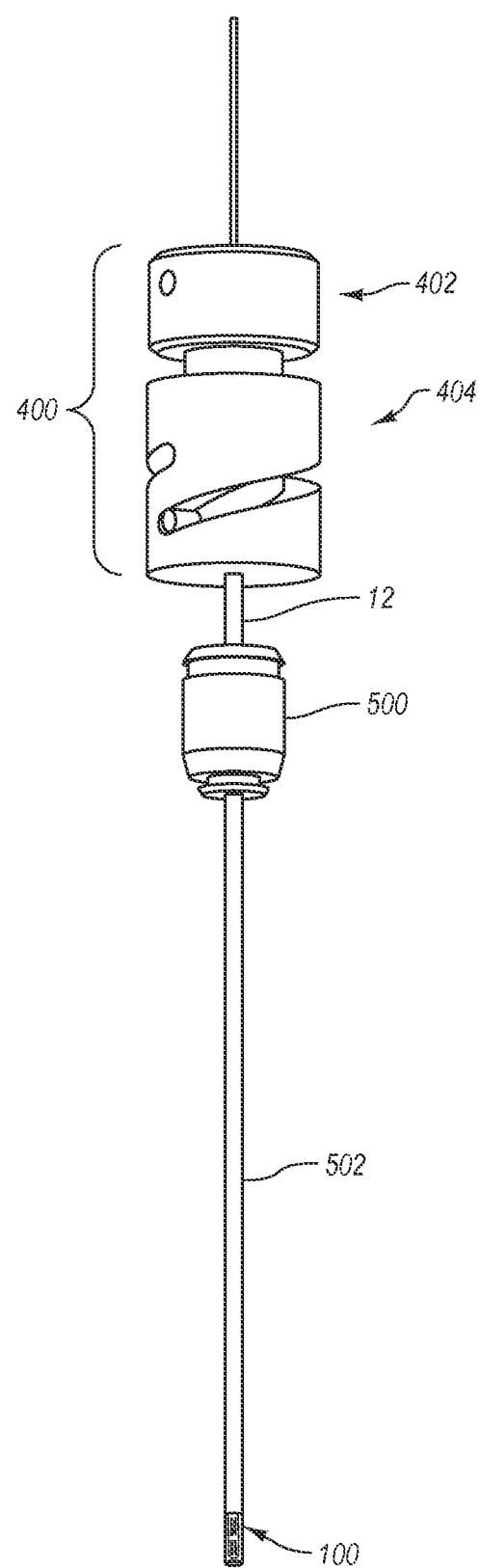
FIG. 13G is a perspective illustration of the delivery system of FIG. 13A in combination with an introducer sheath according to another embodiment of the present invention.

In one specific embodiment, the closure element 100 with the handle assembly 400 cooperates with an introducer sheath 500, as illustrated in FIG. 13G. The introducer sheath 500 may include an introducer elongate member 502. The elongate member 12 and the closure element 100 are passed through the introducer sheath 500 and extend through the introducer elongate member 502 such that the closure element 100 protrudes from the distal end of the introducer elongate member 502. In one example embodiment, the closure element 100 has the distal slits protruding from the introducer elongate member 502.

In operation, the introducer sheath 500 may already be positioned such that the introducer elongate member 502 is located at least partially within the body lumen or extended through an opening in a body lumen wall. The closure element 100, along with the elongate member 12, may then be introduced into the introducer sheath 500 and positioned within the opening in the body lumen. With the closure device located within the introducer sheath 500, the handle element 402 may be rotated such that the actuator 22 is pulled in the proximal direction and the lower or distal region of the closure element 100 changes from a delivery configuration to a deployed configuration, as shown in FIG. 13E.

After the first portion of the closure element has been deployed, the introducer sheath 500 and the introducer elongate member 502 may be moved in the proximal direction such as to uncover the proximal slits 110. At this point, the handle element 402 may be again twisted or rotated such that the actuator 22 is moved or pulled in the proximal direction, thus deploying the upper portion of the closure element 100, as shown in FIG. 13F.

The amount of rotation that may be needed to deploy the closure element 100 or change the closure element 100 from a delivery configuration to a deployed configuration may vary. In one example embodiment, the handle element 402 may be turned one half of a turn to deploy the first portion of the closure element 100 and then turned another half of a turn to deploy the second portion of the closure element 100. However, in other example embodiments it is understood that larger or smaller rotation may be used to deploy the closure element 100.

Once the closure element 100 is deployed and in place within the body lumen wall, the remainder of the closure device and the introducer sheath can be removed in a similar manner as described with respect to FIGS. 3-6.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. It shall be further understood that although the present invention has been described in relation to vessel closure, it is contemplated that the closure component of the present invention may be utilized to close other openings in the body such as PFO openings, or openings formed in organs such as the stomach for certain surgical procedures.

What is claimed is:

1. A method of closing an opening in a blood vessel, the method comprising:
   inserting a closure device at least partially through the opening and into the blood vessel, the closure device including a delivery tube, an actuator, and a closure element, the closure element comprising a body having a proximal portion, a distal portion, and a waist portion, a distal end of the delivery tube being configured with a bias and applies a radial compressive force to the closure element;
   reconfiguring the distal portion of the closure element from a pre-deployed configuration to a deployed configuration, by pulling a distal end of the closure element in a proximal direction, while maintaining the proximal portion of the closure device in a pre-deployed configuration, wherein in the deployed configuration, one or more extensions of the distal portion protrude outward from the body beyond an outer edge of the opening in the blood vessel;
   engaging an inside portion of the blood vessel distally from the opening in the blood vessel with the distal portion of the closure device by moving the closure device in a proximal direction;
   following engaging the inside portion of the opening in the blood vessel, deploying the proximal portion of the closure element from the delivery tube;
   reconfiguring the proximal portion of the closure element from the pre-deployed configuration to a deployed configuration by collapsing a collapsible portion of the body in an outward direction, wherein in the deployed configuration, one or more extensions of the proximal portion protrude outward from the body to engage an outside portion of the blood vessel proximally from the opening in the blood vessel; and
   locking the proximal portion and the distal portion of the closure element in the deployed configuration by advancing a locking element formed on the actuator through a lumen of the proximal portion.

2. The method recited in claim 1, wherein the locking element is tapered from a proximal end to a distal end.

3. The method according to claim 1, further comprising deploying a hemostatic material on or adjacent to the opening in the blood vessel.

4. The method recited in claim 1, further comprising disengaging the delivery tube and actuator from the closure element and removing the delivery tube and actuator.

5. The method recited in claim 1, further comprising holding the proximal end of the closure device between the locking element and a coupler element, the coupler element being coupled to or incorporated with the actuator.

6. The method recited in claim 1, further comprising severing the actuator proximally to the locking element.

7. The method recited in claim 1, wherein reconfiguring the proximal portion of the closure element from the pre-deployed configuration to the deployed configuration further comprises:
   compressively restraining the proximal portion of the closure device within the delivery tube, thereby preventing the collapsible portion of the body from collapsing in the outward direction after the locking element is pulled out of the proximal portion of the closure device; and
   releasing the proximal portion of the closure device from the delivery tube, thereby collapsing the collapsible portion of the body and reconfiguring the proximal portion of the closure device to the deployed configuration.

8. The method of claim 1, further comprising positioning the closure device at a predetermined depth within the delivery tube with at least a portion of the closure device extending beyond the distal end of the delivery tube.

9. The method of claim 8, wherein the predetermined depth is set by a protrusion that limits the insertion of the closure device within the delivery tube.

10. A method of closing an opening in a blood vessel, the method comprising:

inserting a closure device at least partially through the opening, the closure device including a delivery tube, an actuator, and a closure element, the closure element comprising a body having a proximal portion, a distal portion, and a waist portion, a portion of the distal portion of the closure element extending distally from a delivery tube distalmost end prior to inserting the closure device at least partially through the opening, and the proximal portion of the closure element being disposed, within the delivery tube prior to inserting the closure device at least partially through the opening, adjacent a blocking protrusion disposed within a lumen of the delivery tube that prevents proximal movement of the closure device within the lumen of the delivery tube;

reconfiguring the distal portion of the closure element from a pre-deployed configuration to a deployed configuration, by pulling the distal end of the closure element in a proximal direction, while maintaining the proximal portion of the closure device in a pre-deployed configuration, wherein in the deployed configuration, one or more extensions of the distal portion protrude outward from the body;

engaging the inside portion of the opening in the blood vessel with the distal portion of the closure device by moving the closure device in a proximal direction; and reconfiguring the proximal portion of the closure element from the pre-deployed configuration to a deployed configuration by collapsing a collapsible portion of the body in an outward direction, wherein in the deployed configuration, one or more extensions of the proximal portion protrude outward from the body.

11. The method recited in claim 10, further comprising locking the distal portion and the proximal portion of the closure element in their respective deployed configurations.

12. The method according to claim 10, further comprising deploying a hemostatic material on or adjacent to the opening in the blood vessel.

13. The method recited in claim 10, further comprising disengaging the delivery tube and actuator from the closure element and removing the delivery tube and actuator.

14. The method recited in claim 10, wherein collapsing a portion of the body comprises pulling a locking element through and out of the proximal portion of the closure device, the locking element being coupled to or incorporated with the actuator and being configured to collapse the collapsible portion of the body in the outward direction.

15. The method recited in claim 14, further comprising holding the proximal end of the closure device between the locking element and a coupler element, the coupler element being coupled to or incorporated with the actuator.

16. The method recited in claim 14, further comprising severing the actuator proximally to the locking element.

17. The method recited in claim 14, wherein reconfiguring the proximal portion of the closure element from the pre-deployed configuration to the deployed configuration further comprises:

compressively restraining the proximal portion of the closure device within the delivery tube, thereby preventing the collapsible portion of the body from collapsing in the outward direction after the locking element is pulled out of the proximal portion of the closure device; and releasing the proximal portion of the closure device from the delivery tube, thereby collapsing the collapsible portion of the body and reconfiguring the proximal portion of the closure device to the deployed configuration.

18. The method of claim 10, further comprising positioning the closure device at a predetermined depth within the delivery tube.

19. The method of claim 18, wherein the predetermined depth is set by a protrusion that limits the insertion of the closure device within the delivery tube.

* * * * *